United States Patent [19]

Fasig et al.

[11] Patent Number: 5,663,710

[45] Date of Patent: Sep. 2, 1997

[54] BACKSCATTER-TYPE VISIBILITY DETECTION

[75] Inventors: Harold A. Fasig; Charles E. Mallon; Raymond Denson; James R. Fasig, all of San Diego; Peter G. Coakley, Cardiff; Steven W. Lutjens, San Diego; Terry M. Flanagan, Los Angeles; Edward J. Vasel, San Diego, all of Calif.

[73] Assignee: Jaycor, San Diego, Calif.

[21] Appl. No.: 503,994

[22] Filed: Jul. 18, 1995

[51] Int. Cl.⁶ .................................................. G01W 1/00
[52] U.S. Cl. .......................... 340/601; 340/602; 340/905; 340/583; 250/338.1; 250/338.5; 250/341.8
[58] Field of Search ........................ 340/601, 602, 340/901, 904, 905, 968, 584, 583, 903; 73/170.16; 342/26, 53; 250/338.5, 341.8, 339.1, 338.1

[56] References Cited

U.S. PATENT DOCUMENTS

| | | | |
|---|---|---|---|
| 3,704,461 | 11/1972 | Rose et al. | 340/258 B |
| 3,901,812 | 8/1975 | Hallengren | 250/565 |
| 4,282,527 | 8/1981 | Windermann et al. | 343/725 |
| 4,628,301 | 12/1986 | Brown et al. | 340/584 |
| 4,636,643 | 1/1987 | Nakamura et al. | 250/338.1 |
| 4,737,629 | 4/1988 | Inama | 340/601 |
| 4,754,149 | 6/1988 | Wang | 250/573 |
| 4,867,561 | 9/1989 | Fujii et al. | 356/237 |
| 4,874,242 | 10/1989 | Bezard et al. | 340/602 |
| 4,925,310 | 5/1990 | Feppon et al. | 356/434 |
| 4,931,767 | 6/1990 | Albrecht et al. | 340/601 |
| 5,349,267 | 9/1994 | Brassier et al. | 315/82 |

OTHER PUBLICATIONS

"Report No. 512; Project 792104/001–003; Fog Detectors for Unmanned Aids to Navigation", *U.S. Coast Guard Office of Research and Development, Washington D.C.* (Jul. 17, 1970).

Lifsitz, et al., "Fog Bank Detector Field Tests: A Technical Summary", *Transportation Systems Center, Cambridge Mass.*, pp. 1–32, (Dec. 1971).

"Automatic Fog Alert System Protects Busy Highway", *Rural and Urban Roads*, p. 36 (May 1973).

"Airport Lights Shine on Fog–Bound Highway", *American City & County*, pp. 35–36 (Jan. 1980).

"Fog Detectors Warn Drivers of Low Visibility", excerpt from *Machine Design*, p. 30 (Feb. 8, 1990).

"Infrared Lasers Prevent Crashes: The Anti–Collision Fog System Makes for Safer Driving", *New–Tech News*, pp. 30–32 (Jan. 1992).

*Primary Examiner*—Brent A. Swarthout
*Assistant Examiner*—Van T. Trieu
*Attorney, Agent, or Firm*—Fitch, Even, Tabin & Flannery

[57] ABSTRACT

An improved visibility detector and method emit infrared radiation away from an infrared emitter; detect an amount of infrared radiation backscattered by an airborne visibility impeding agent; and generate a backscatter signal in response to the amount detected. In one embodiment, the detector detects an amount of the infrared radiation that is not backscattered; generates a reference signal in response thereto; determines an actual amount of the infrared radiation backscattered; determines whether the actual amount exceeds a prescribed threshold; and generates an alarm signal in event the actual amount is determined to exceed the prescribed threshold. In other embodiments, the device employs a meniscus barrier between the emitter and the detector; another, lower, threshold in determining when to terminate the alarm signal; a second alarm signal to indicate that backscatter has increased above another, higher, threshold; a calibration scheme for calibrating the detector and/or a running average to avoid anomalous indications of low/high visibility.

23 Claims, 13 Drawing Sheets

BACKSCATTER-TYPE VISIBILITY DETECTION

BACKGROUND OF THE INVENTION

The present invention relates to visibility detection, and more particularly to detection of airborne visibility impairing or impeding agents. Even more particularly, the present invention relates to improvements in detection of such agents using backscattered infrared radiation (or light).

Fog, heavy rain, sleet, snow, sand and dust are among airborne agents that can cause reduced or impaired visibility on roadways. When present, they are likely to produce unpredictable and dangerous driving conditions. Drivers, perhaps fearing rear-end collisions, blindly proceed into these elements at high speeds. Visibility distance is frequently less than the stopping distance for these vehicles, making it impossible to these drivers to perceive a hazard in time to avoid it by stopping. Every year, news stories abound detailing multiple-vehicle collisions, caused by the "piling-up" of vehicle after vehicle under these dangerous conditions.

Systems have been proposed for detecting fog using an infrared emitter/detector pair for "diffusing" infrared radiation, and for detecting "retrodiffusion" (diffusion back toward the emitter/detector pair). Such systems have been mounted in a vehicle and used to activate and deactivate fog lamps, see U.S. Pat. No. 5,349,267 of Brassier et al., and have been mounted in a wayside (i.e., roadside) housing and used to illuminate flashing warning signs, see "Automatic Fog Alert System Protects Busy Highway," Rural and Urban Roads, Vol. 11 N, No. 5; and "Infrared Device Detects Fog," Public Works, Vol. 104, No. 4. A similar wayside detection system has been used to illuminate lights marking outside edges of pavement. See "Airport Lights Shine on Fog-Bound Highway," American City and County, Vol. 95, No. 6. In another system, infrared lasers and detectors mounted in a vehicle are used to detect a visibility range by measuring backscatter. See "Infrared Lasers Prevent Crashes: The Anti-collision Fog System Makes for Safer Driving," NEW-TECH NEWS, No. 1–19.

Unfortunately, the above-described wayside detection systems fail to address several important problems. For example, in the event the field of vision of the emitter or detector becomes impaired due to the buildup of dust, and/or "road dirt," such as brake pad particles, tire particles or airborne oil particles, on an emitter lens or detector lens, the detector may indicate that fog does not exist (i.e., that there is little or no backscattered infrared radiation detected), when in fact visibility is fog-impaired (i.e., there is significant backscattered infrared radiation). One potential solution that may be adaptable to a wayside system is proposed in the NEW-TECH article, cited above, which describes the use of a wiper, similar to a windshield wiper. Problematically however, even if the wiper could be adapted for use in a wayside system, it still does not assure that the field of view is not impaired—rather it only attempts to mechanically remove any impairment that might be impairing the field of view. Furthermore, in that the use of a wiper implies the use of motor to turn the wiper, an undesireably high current is required to operate the wiper. While such current is readily available in an automobile, it may not be available in a wayside system, which preferably could be powered by a solar-recharged battery.

The above mentioned heretofore known visibility detectors rely on the fact that fog and other agents reflect, retrodiffuse or backscatter infrared light directed into a fog bank or other area of high visibility inhibiting agent concentration.. Unfortunately, fog and other airborne visibility reducing agents are not of a constant density, i.e., they may be concentrated in pockets, may billow and may be affected by gusts of wind. As a result, the density of the fog, or other visibility reducing agent, may vary locally even though visibility overall remains low. The above-described visibility detection systems, as described in the above-cited documents, fail to account for this quality, and as a result are subject to falsely or prematurely detecting that visibility has been restored, or that visibility has been reduced, in response to pockets of visibility or pockets of, e.g., fog. Thus, the lights controlled by the above-mentioned wayside systems will be controlled by the emitter/detector pair to illuminate and extinguish as pockets of clear and pockets of, e.g., fog, pass over the emitter/detector pair. Such will occur even though the roadway may be predominantly clear or, e.g., predominantly foggy.

One solution to the problem of false detection is described in the '267 patent, wherein in order to prevent inappropriate illumination or extinction of a fog lamp, a time delay module is arranged on the output of a comparator. As a result, the emitter/detector pair of the '267 patent must detect adequate visibility or inadequate visibility for a predetermined time period before signaling an indication of such to circuity controlling the illumination and extinction of the foglamps. Unfortunately, if adequate visibility has been restored (after a period of inadequate visibility), but small pockets of poor visibility continue to pass over the emitter/detector pair; or if visibility has become inadequate (after a period of adequate visibility), but pockets of clear continue to pass over the emitter/detector pair, the visibility detector of the '267 patent will continue to signal an inappropriate illumination or extinction, so long as such pockets pass over the emitter/transmitter pair at an interval shorter than the prescribed time delay. If the prescribed time delay is shortened to avoid this prolonged erroneous illumination or extinction, the emitter/detector pair may signal an illumination every time a pocket of impaired visibility passes, or an extinction every time a pocket of clear passes, so long as such pockets are large enough to increase or reduce backscatter for the shortened time delay.

A further problem with the above-mentioned heretofore known visibility detectors, as described in the above-cited references, is calibration. In the '267 patent, for example, the visibility detector is calibrated either using a potentiometer to adjust a reference threshold and/or using a secondary detector to a detect degree of pollution, atmospheric pressure, and ambient temperature. Unfortunately, such a calibration scheme, if it could be used with a wayside visibility detector, requires individual manual adjustment at each emitter/detector at the time of installation, so as to account for environmental retrodiffusion or backscatter as a result of, e.g., trees, guard rails, road signs and the like. Such manual adjustment would require that more highly skilled personnel be utilized for installation, and, because such environmental backscatter changes over time, because, for example, trees change shape and size (and therefore amount of backscatter) as they grow, periodic manual adjustment of such a wayside visibility detector unfortunately would be necessary.

One major problem not recognized in any of the above-mentioned references is meniscus conduction of infrared radiation from the emitter to the transmitter. Meniscus conduction occurs when a layer of water adheres to the surface of the emitter or emitter lens, the detector or detector lens, and a housing surface interposed between them. When infrared light is emitted from the emitter, some of it is diffused away from the emitter. However, when the layer of water (i.e., meniscus) is present, some of the emitted infrared light is reflected or diffused by the surface of the layer of water and is conducted by the water away from the emitter across the interposed surface of the housing to the detector. Problematically, such conducted infrared light is interpreted by the detector to be backscattered infrared light, and therefore increases the detected amount of backscatter. In turn, as the detected amount of backscatter increases, the visibility is incorrectly determined by the visibility detector circuitry to have decreased. As a result, when such meniscus conduction occurs, such as may occur during a light rain or mist, or when wayside water sprinklers are activated, the visibility detectors, as described above and in some of the cited references, are prone to indicate that visibility is impaired, when it may not be.

Thus, significant needs in visibility detectors, and in particular in wayside visibility detectors, remain unaddressed by heretofore known visibility detectors. The present invention advantageously addresses the above and other needs.

SUMMARY OF THE INVENTION

The present invention advantageously addresses the needs above as well as other needs by providing an improved visibility detection system and method.

The invention can be characterized, in one embodiment, as a system for detecting an airborne visibility impeding agent. The system employs an infrared emitter for emitting infrared radiation; an infrared backscatter detector positioned to receive a first portion of the infrared radiation, which is backscattered by the airborne visibility impeding agent, and for generating a backscatter signal in response to the detected amount of the first portion; an infrared reference detector positioned to receive a second portion of the infrared radiation, which is not backscattered by the airborne visibility impeding agent, and for generating a reference signal in response to the detected amount of the second portion of infrared radiation; and a visibility determination circuit coupled to the infrared emitter, the infrared backscatter detector and the infrared reference detector. The visibility determination circuit determines a determined amount of the infrared radiation that is backscattered by the airborne visibility impeding agent, and determines whether the determined amount exceeds a prescribed threshold. In the event the determined amount does exceed the prescribed threshold, the visibility determination circuit generates an alarm signal.

In another embodiment, the invention may be characterized as a system employing a housing having a surface; an infrared emitter positioned in the surface, for emitting infrared radiation; an infrared backscatter detector positioned in the surface to receive a portion of the infrared radiation that is backscattered by an airborne visibility impeding agent; a meniscus barrier including a ridge, on the surface, interposed between the infrared emitter and the infrared backscatter detector; and a visibility determination circuit coupled to the infrared emitter and the infrared backscatter detector. The meniscus barrier prevents diffusion of the infrared radiation through a fluid meniscus on the surface between the infrared emitter and the infrared backscatter detector. The visibility determination circuit determines an amount of the infrared radiation that is backscattered by the airborne visibility impeding agent, determines whether the amount determined exceeds a prescribed threshold, and generates an alarm signal in event the amount is determined to exceed the prescribed threshold.

The invention, in a further embodiment, can also be characterized as a method having the steps of emitting infrared radiation away from an infrared emitter; detecting an amount of a first portion of the infrared radiation that is backscattered by an airborne visibility impeding agent; generating a backscatter signal in response to the amount of the first portion detected; detecting an amount of a second portion of the infrared radiation, which is not backscattered by the airborne visibility impeding agent; generating a reference signal in response to the amount of the second portion detected; determining an actual amount of the infrared radiation backscattered by the airborne visibility impeding agent in response to the backscatter signal and the reference signal; determining whether the actual amount exceeds a prescribed threshold; and generating an alarm signal in event the actual amount is determined to exceed the prescribed threshold.

In another embodiment, the invention can be characterized as a method possessing the steps of calibrating and detecting reduced visibility. The calibrating step involves generating a recalibrate signal by e.g. pressing a button; emitting infrared radiation that radiates away from an infrared emitter, in response to the recalibrate signal; detecting a baseline amount of the infrared radiation that is backscattered; generating a calibration signal in response to the baseline amount; and determining a prescribed threshold as a function of the calibration signal. The step of determining reduced visibility involves emitting infrared radiation away from the infrared emitter; detecting a detected amount of the infrared radiation that is backscattered by an airborne visibility impeding agent; generating a detection signal in response to the detected amount of the infrared radiation; determining whether the detection signal exceeds the prescribed threshold; and generating an alarm signal in event the detection signal is determined to exceed the prescribed threshold.

Another way in which the invention can be characterized is as a method employing the following steps: detecting a reduced visibility condition, and detecting an increased visibility condition. The step of detecting reduced visibility entails emitting infrared radiation away from an infrared emitter; detecting a first amount of the infrared radiation, which is backscattered by an airborne visibility impeding agent; generating a first detection signal in response to the first amount of the infrared radiation; determining whether the first amount exceeds a first prescribed threshold; and generating an alarm signal in event the first amount is determined to exceed the first prescribed threshold. The step of detecting an increased visibility condition includes emitting infrared radiation away from the infrared emitter; detecting a second amount of infrared radiation, which is backscattered by the airborne visibility impeding agent; generating a second detection signal in response to the second amount of the infrared radiation; determining whether the second amount is less than a second prescribed threshold, which is lower than the first prescribed threshold, i.e., corresponds with a smaller amount of backscattered infrared radiation); and terminating the alarm signal in event the second amount is determined to be less than the second prescribed threshold.

The invention can also be characterized, in a further embodiment, as method employing steps of emitting infrared radiation away from an infrared emitter; detecting an amount of the infrared radiation that is backscattered by an airborne visibility impeding agent; generating a detection signal in response to the amount of the infrared radiation detected; determining whether the detection signal exceeds a first prescribed threshold; generating a first alarm signal in event the detection signal is determined to exceed the first prescribed threshold; determining whether the detection signal exceeds a second prescribed threshold (that is higher than the first prescribed threshold, i.e., corresponds to a higher amount of backscattered radiation); and generating a second alarm signal in the event the detection signal is determined to exceed the second prescribed threshold.

In another embodiment, the invention can be characterized as a method having steps of emitting infrared radiation away from an infrared emitter; detecting an amount of the infrared radiation that is backscattered by an airborne visibility impeding agent; generating a backscatter signal in response to the amount of the infrared radiation detected; then repeating the emitting, the detecting and the generating at least two times. Next, the present method includes determining a running average of the backscatter signal over time; determining whether the running average exceeds a prescribed threshold; and producing an alarm signal in event the running average is determined to exceed the prescribed threshold.

Thus, it is a feature of the invention to provide improvements in the detection of visibility conditions.

It is another feature of the invention to detect visibility conditions by comparing an amount of backscattered infrared radiation with a prescribed threshold.

It is a further feature of the invention, in some embodiments, to scale the amount of backscattered infrared radiation using a reference amount of infrared radiation originating from the same radiation source as the backscattered infrared radiation.

It is an additional feature of the invention, in some embodiments, to provide for the generation of an alarm signal in the event visibility falls below the prescribed threshold.

It is an added feature of the invention, in some embodiments, to terminate the alarm signal only when visibility increases above another, higher, threshold.

It is a supplementary feature of the invention, in some embodiments, to minimize the effects of anomalous backscatter amounts, such as might be caused by small pockets, puffs or billows of visibility impeding agent and/or by small pockets, puffs or billows of clear air, by maintaining a running average of, e.g., the last ten backscatter detections, and comparing the running average, instead of the amount of backscatter detected, to the prescribed threshold (and, possibly, the other, higher, threshold).

It is another added feature of the invention, in some embodiments, to provide for the generation of another alarm signal the event visibility falls below another, lower, threshold.

It is another further feature of the invention, in some embodiments, to provide a meniscus barrier between an infrared emitter and an infrared backscatter detector that prevents conduction of infrared radiation through a fluid meniscus that may form between the infrared emitter and the infrared backscatter detector.

Numerous other embodiments of the invention are also envisioned by the inventors, and will be appreciated by those of skill in the art based on the descriptions made herein and the appended claims.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description of the presently contemplated best mode of practicing the invention is not to be taken in a limiting sense, but is made merely for the purpose of describing the general principles of the invention. The scope of the invention should be determined with reference to the claims.

Figure 1:
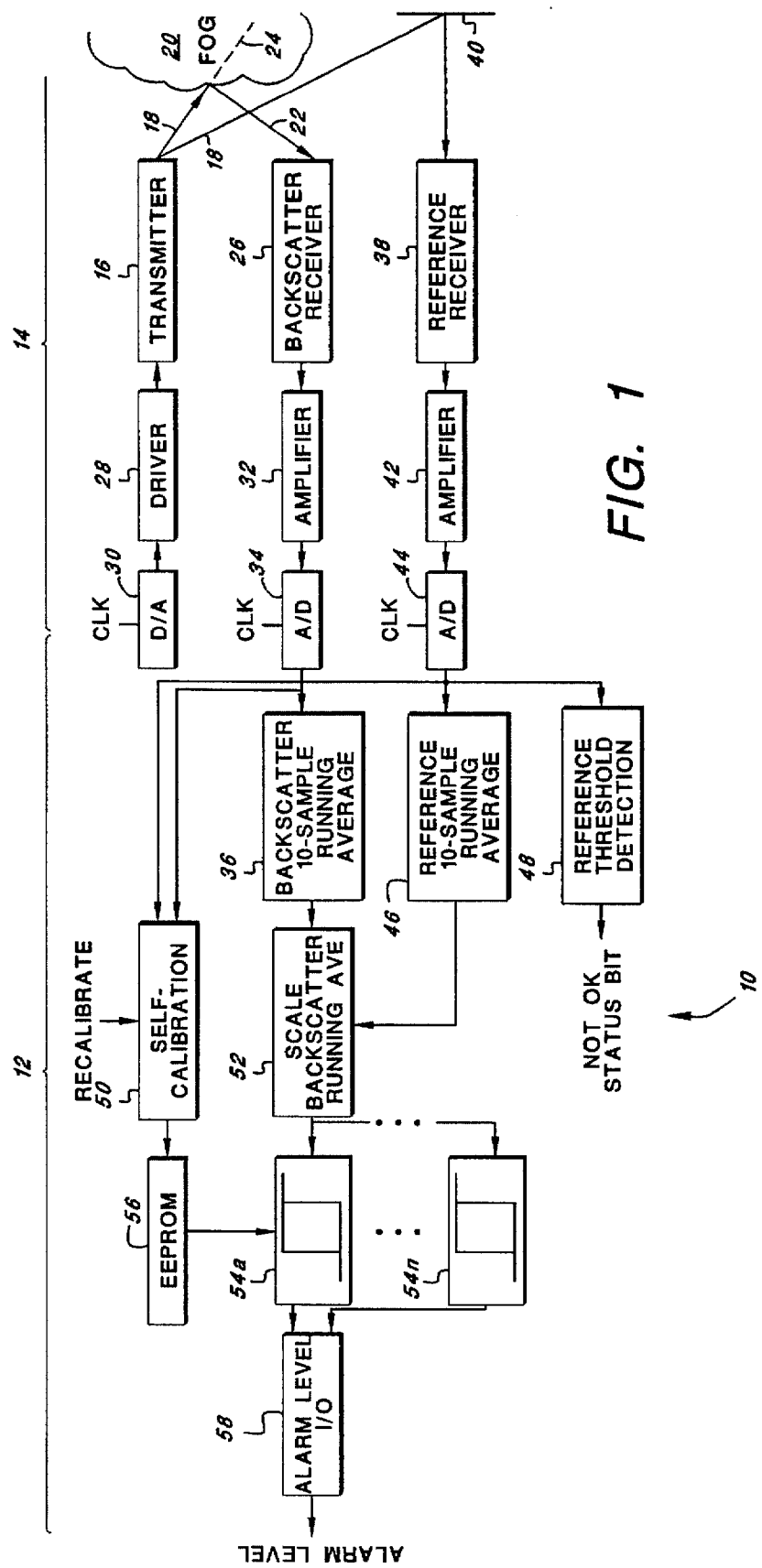
FIG. 1 is a block diagram showing the functional components of one embodiment of a backscatter-type visibility detector made in accordance with the present invention.

Referring first to FIG. 1, a block diagram is shown illustrating the functional components of one embodiment of a backscatter-type visibility detection system 10 made in accordance with the present invention; a digital section 12, and an analog section 14 are shown. The analog section 14 includes an infrared emitter (or transmitter) such as Part No. OD-663 available from Opto Diode Corporation of Newbury Park, Calif. The transmitter 16 generates infrared radiation 18 having an intensity of 2 watts and a wavelength of 880 nm. As can be seen, the infrared radiation 18 is directed away from the transmitter 16 so that it impinges upon any airborne visibility inhibiting (or impeding) agents 20 that are present in the atmosphere near the backscatter-type visibility detection system 10. One example of an airborne visibility inhibiting agent 20, i.e., fog, is shown. The infrared radiation 18 is in part 22 reflected by the fog and is in part 24 transmitted by the fog 20. The amount of reflection (or backscatter) is a function of the density of the fog 20 (or other airborne visibility inhibiting agent). Also shown is a backscatter receiver 26 (or detector) that receives backscattered part of the infrared radiation 22. The backscatter receiver 26, which may be Part No. OSI-1193A available from Opto Sensors, Inc. of Torrance, Calif., generates a backscatter signal in response to the amount of backscattered infrared radiation 22 detected. The backscatter signal may, for example, vary in voltage as a function of the amount of backscattered infrared radiation 22 detected.

Because the amount of backscattered radiation 22 is a function of the amount of airborne visibility inhibiting agent 20 present in the atmosphere near the transmitter 16 and near the receiver 26, the backscatter signal is, in turn, a function of the amount of airborne visibility inhibiting agent 20 present in the atmosphere. In this way, the infrared transmitter 16 and the backscatter receiver 26, in generating the backscatter signal, provide an indication to the backscatter-type visibility detection system 10 of the amount of airborne visibility inhibiting agent 20 present in the atmosphere.

The transmitter 16 is coupled to a driver circuit 28, which is in turn coupled to a digital to analog converter 30, which is coupled to a clock circuit (not shown). In response to a periodic signal generated by the clock circuit, the digital to analog converter 30 generates a trigger signal which is passed along to the driver circuit 28. In response to the trigger signal, the driver circuit 28 generates a driver signal that periodically powers the transmitter 16, causing periodic generation of the infrared radiation 18. Thus, pulses of the infrared radiation 18, as opposed to a continuous emission of infrared radiation, are preferably emitted from the transmitter 16 in response to the periodic signal from the clock.

The backscatter receiver 26 is coupled to an amplifier 32 that amplifies the backscatter signal. The amplifier 32 is coupled to an analog-to-digital converter 34, which is coupled to the clock circuit and to a backscatter ten-sample running average computer 36. The analog-to-digital converter 34 digitizes the backscatter signal having been amplified and generates a backscatter 10-sample running average computer 36.

Another infrared receiver 38 (or detector) is also shown and is referred to herein as a reference receiver. The reference receiver 38 is positioned so as to receive infrared radiation 18 transmitted by the transmitter. Unlike the infrared radiation received by the backscatter receiver 26, the radiation received by the reference receiver 38 is not back-scattered by the airborne visibility inhibiting agent 20. Instead, the radiation received by the reference receiver 38 is either directly transmitted from the transmitter 16 to the reference receiver 38, or is reflected (or diffused) using a suitable reflector 40, such as a mirror. As with the backscatter receiver 26, the reference receiver 38 is coupled to an amplifier 42, which is coupled to an analog-to-digital converter 44. The amplifier 42 and analog-to-digital converter 44 coupled to the reference receiver 38, functions in a manner similar to that described above with respect to the amplifier 32 and analog-to-digital converter 34 coupled to the reference receiver 38. The analog-to-digital converter 44 coupled through the amplifier 42 to the reference receiver 38 is also coupled to the clock circuit and to a reference ten-sample running average computer 46. The reference receiver 38 generates a reference signal in response to the amount of infrared radiation received by the reference receiver 38. The reference signal is passed by the reference receiver 38 to the amplifier 42, which amplifies the reference signal, and passes the reference signal along to the analog-to-digital converter 44, which digitizes the reference signal having been amplified and generates a reference sample in response thereto. The reference sample is passed along to the reference ten-sample running average computer 46.

Together, the digital-to-analog converters 34, 44 and amplifiers 32, 42, the driver 28, the digital to analog converter 30, the transmitter 16, the backscatter receiver 26, and the reference receiver 38 comprise the analog portion 14 of the backscatter-type visibility detection system 10.

The digital portion 12 of the backscatter-type visibility detection system 10 comprises the backscatter ten-sample running average computer 36, and the reference ten-sample running average computer 46. In addition, a reference threshold detection system 48, a self-calibration system 50, a backscatter running average scaler 52, hysteresis-type threshold detectors 54a through 54n, an electronically erasable programmable read only memory 56 (EEPROM) and an alarm level signal generator 58 are part of the digital portion 12 of the backscatter-type visibility detection system. The backscatter ten-sample running average computer 36 and the reference ten-sample running average computer 46 are coupled to the backscatter running average scaler 52, and the reference threshold detection system 48 is coupled to the analog-to-digital converter 44 coupled to the reference receiver 38. The self-calibration system 50 is coupled to both the analog-to-digital converter 34 coupled to the backscatter receiver 26, and the analog-to-digital converter 44 coupled to the reference receiver 38. The EEPROM 56 is coupled to the self-calibration system 50. The alarm level signal generator 58 is coupled to each of the hysteresis threshold detectors 54a through 54n, and each of the hysteresis threshold detectors 54a through 54n are coupled to the EEPROM 56, and to the backscatter running average scaler 52.

In response to the backscatter sample generated by the analog-to-digital converter 34 coupled to the backscatter receiver 26, the backscatter ten-sample running computer 36 calculates a ten-sample running average of the backscatter signal samples. This is done by computing the average magnitude of the ten most recent backscatter signal samples generated by the analog-to-digital converter 34. As new backscatter signal samples are generated, they are included in new ten-sample running average calculations. The reference ten-sample running average computer 46 generates a reference ten-sample running average in a similar manner in response to the reference signal samples generated by the analog-to-digital converter 44 coupled to the reference receiver 38. Both the backscatter ten-sample running average and the reference ten-sample running average are passed along to the backscatter running average scaler 52.

Using the reference ten-sample running average, the backscatter running average scaler scales the backscatter ten-sample running average so as to eliminate the effects of, for example, temperature and contaminant buildup on the backscatter receiver 26 (which is presumed to be about the same contaminant buildup, and temperature, as the reference receiver 38). In this way, the effects of contaminant buildup, and temperature, are effectively eliminated from the backscatter ten-sample running average.

The reference threshold detection system 48 monitors the reference signal samples generated by the analog-to-digital converter 44 coupled to the reference receiver 38. If the amount of infrared radiation incident on the reference receiver 38, as indicated by the reference signal samples, falls below a prescribed threshold, the reference threshold detection system 48 generates a "NOT OK" status bit indicating that the backscatter-type visibility detection system 10 may not be generating accurate information on the amount of airborne visibility inhibiting agents 20 in the atmosphere. In response to the NOT OK status bit being set, appropriate output signals are generated so as to notify the persons responsible for maintaining the backscatter-type visibility detection system 10 that some aspect of the backscatter-type visibility detection system 10 requires their attention. One example of a condition that commonly causes the NOT OK status bit to be set is the buildup of excessive contaminants on the reference receiver 38. When such contaminants buildup, the reference receiver 38 detects little or no infrared radiation from the transmitter 16, even though, in the present embodiment, the infrared radiation incident on the reference receiver 38 is always significant enough to be detected.

Advantageously, because the reference receiver 38 and the backscatter receiver 26 are preferably positioned near to one another so as to be exposed to similar amounts of contaminants, such as "road dirt", including oil, tire particles, and break pad particles, the detection of excessive buildup of contaminants on the surface of the reference receiver 38 also suggests that such contaminants have built up on the backscatter receiver 26. Because when the backscatter receiver 26 is covered with an excessive amount of contaminants it is unable to receive infrared radiation 22 having been backscattered by airborne visibility inhibiting agents 20, it will generate a backscatter signal indicating that little or no backscatter is occurring. This happens even though a significant amount of backscatter may be occurring, creating a potentially dangerous situation, in that when such significant amount of backscatter is occurring, it is likely that there is a significant amount of airborne visibility inhibiting agents 20 present in the atmosphere. The failure to detect such a high concentration of airborne visibility reducing agents may result in the failure of the backscatter-type visibility detection system 10 to signal that a low visibility condition exists, thus resulting in a failure of the backscatter-type visibility detection system 10 to perform its most important function.

The self-calibration system 50 receives the backscatter signal samples and the reference signal samples from the two analog-to-digital converters 34, 44. Normally, the self-calibration system 50 is inactive, and ignores the output of these two analog-to-digital converters 34, 44. Upon the generation of a recalibration signal, which is passed to the self-calibration system 50, the self-calibration system 50 computes a plurality of thresholds used by the hysteresis threshold detectors 54a through 54n. These thresholds are stored in the EEPROM 56. The recalibration signal is generated in one of several different ways. For example, the recalibration signal can be generated in response to the depression of a single pole single throw (SPST) momentary switch (not shown) located within the housing that houses the backscatter-type visibility detection system 10. Alternatively, the recalibration signal may be generated in response to a command issued to the backscatter-type visibility detection system 10 by an external programmer, such as a personal computer or laptop computer. Generation of the recalibration signal in this manner is explained more fully below.

In the present embodiment, the recalibration signal should only be generated when the atmosphere near the transmitter 16 and backscatter receiver 26, contains little or no airborne visibility inhibiting agents 20, i.e., When it is clear. In this way, generation of the recalibration signal indicates to the backscatter-type visibility detection system 10 that high visibility or clear conditions exist, and causes the self-calibration system 50 to read the backscatter sample and receiver sample as a baseline indication of visibility. As visibility decreases from this baseline, the backscatter-type visibility detection system 10 is able to determine the reduction in visibility relative to this baseline by measuring an increase in backscattered radiation 22.

It is important to note that this baseline is a function not only of the amount of airborne visibility inhibiting agents present in the atmosphere surrounding the transmitter 16 and the backscatter receiver 26 when visibility conditions are generally clear, but also a function of background items such as trees, roadway guardrails and road signs. For this reason, it is impossible to conduct calibration of the backscatter-type visibility detection system before placing the system at the location where it will ultimately operate. Advantageously, calibration of the present embodiment is achieved merely by pressing a button, or by issuing a command from an external programming device. Thus, unlike heretofore known backscatter-type visibility detection systems, the present embodiment can quickly and easily be calibrated by a technician with little or no understanding of the internal workings of the backscatter-type visibility detection system 10 of the present embodiment.

The determined baseline is used by the self calibration system 50, as mentioned above, to generate a plurality of thresholds. In its simplest form, the present embodiment utilizes two thresholds: an upper threshold and a lower threshold. The lower threshold, which corresponds to a higher visibility level, i.e., a "lower" amount of backscattered infrared radiation, than the upper threshold, is used by one of the hysteresis threshold detectors 54a to determine the level of visibility at which an indication of low or poor visibility should be made. The upper threshold, in contrast, is used by the hysteresis threshold detector 54a to determine the level of visibility at which an indication of low visibility should be made, i.e., a "higher" amount of backscattered infrared radiation. The hysteresis threshold detector 54a makes these determinations by comparing the backscatter ten-sample running average, having been scaled by the backscatter running average scaler 52, with each of these thresholds. When visibility is high and then begins to decrease, the scaled backscatter ten-sample running average will indicate such decrease by signaling an increase in backscattered infrared radiation. The amount of backscattered infrared radiation reaches a level indicative of a low visibility condition (as defined by the upper threshold), when the scaled backscattered ten-sample running average exceeds the upper threshold. In response to the increasing of the scaled backscatter ten-sampled running average to above the upper threshold, the hysteresis threshold detector 54a generates an alarm condition signal signifying that visibility is low. Subsequently, as visibility begins to increase, the amount of backscattered infrared radiation decreases, and this is reflected in the scaled backscatter ten-sample running average. As the scaled backscatter ten-sample running average decreases below the upper threshold, the alarm signal continues to be generated by the hysteresis threshold detector 54a. As the scaled backscatter ten-sample running average then continues to decrease below the lower threshold, the hysteresis threshold detector 54a stops generating the alarm signal.

The alarm signal, when generated, is passed to the alarm level signal generator 58, which generates an alarm level signal in response to the alarm signal and passes it along to external circuits, such as a cellular telephone transceiver or electrical switching apparatuses (that, for example, illuminate a fog warning light or sign), or the like.

In an alternative embodiment, multiple threshold levels are computed by the self-calibration system 50 and stored in the EEPROM 56. These multiple threshold levels are utilized by a plurality of hysteresis threshold detectors 54a through 54n, each of which generate alarm signals indicative of visibility levels within respective prescribed ranges. These hysteresis threshold detectors are all coupled to the alarm level signal generator 58 which encodes the alarm signals into the alarm level signal. The alarm level signal is then passed along to the external circuits.

In this way, the present embodiment is able to determine the presence of high or low visibility or alternatively, of a multiplicity of visibility levels, in response to the amount of infrared radiation backscattered by an airborne visibility inhibiting agent. Advantageously, the present embodiment utilizes the reference receiver 38 so as to eliminate the effects of, e.g., temperature and contaminant buildup on the backscatter receiver 26, and reference receiver 38. The present embodiment also employs the backscatter ten-sample running computer average 36, and the reference ten-sample running average computer 46 so as to smooth out momentary increases or decreases in the amount of infrared radiation detected, such as can result, for example, from pockets of clear air within an otherwise low visibility atmosphere containing airborne visibility inhibiting agents. The running averages generated by these two ten-sample running average computers 36, 46 are used to generate a scaled backscatter ten-sample running average (which, as mentioned above, eliminates the effects of, e.g., temperature and contaminant buildup). A hysteresis threshold detector 54a, or alternatively, a plurality of such detectors 54a through 54n, are then utilized to stop and start the generation of one or more alarm signals. Use of the hysteresis feature of the hysteresis threshold detectors 54a through 54n further reduces the impact of clear areas, or billowing, in the airborne visibility inhibiting agent 20.

Advantageously, the present embodiment utilizes the self-calibration system 50 to determine a baseline level of backscattered infrared radiation. This baseline level is determined in response to the depression of a button or in response to a command from an external programmer, and is preferably determined after the backscatter-type visibility detection system is in place at the location where it will operate. No fine tuning or sophisticated adjustment of the backscatter-type visibility detection system 10 is necessary at such location.

A further advantage of the present embodiment is realized through the use of the reference threshold detection circuit 48, which serves to notify those responsible for maintaining the backscatter-type visibility detection system 10 of a need for servicing, such as the cleaning of the backscatter receiver 26, and the reference receiver 38 of contaminants such as oil, brake dust, or tire dust.

Figure 2:
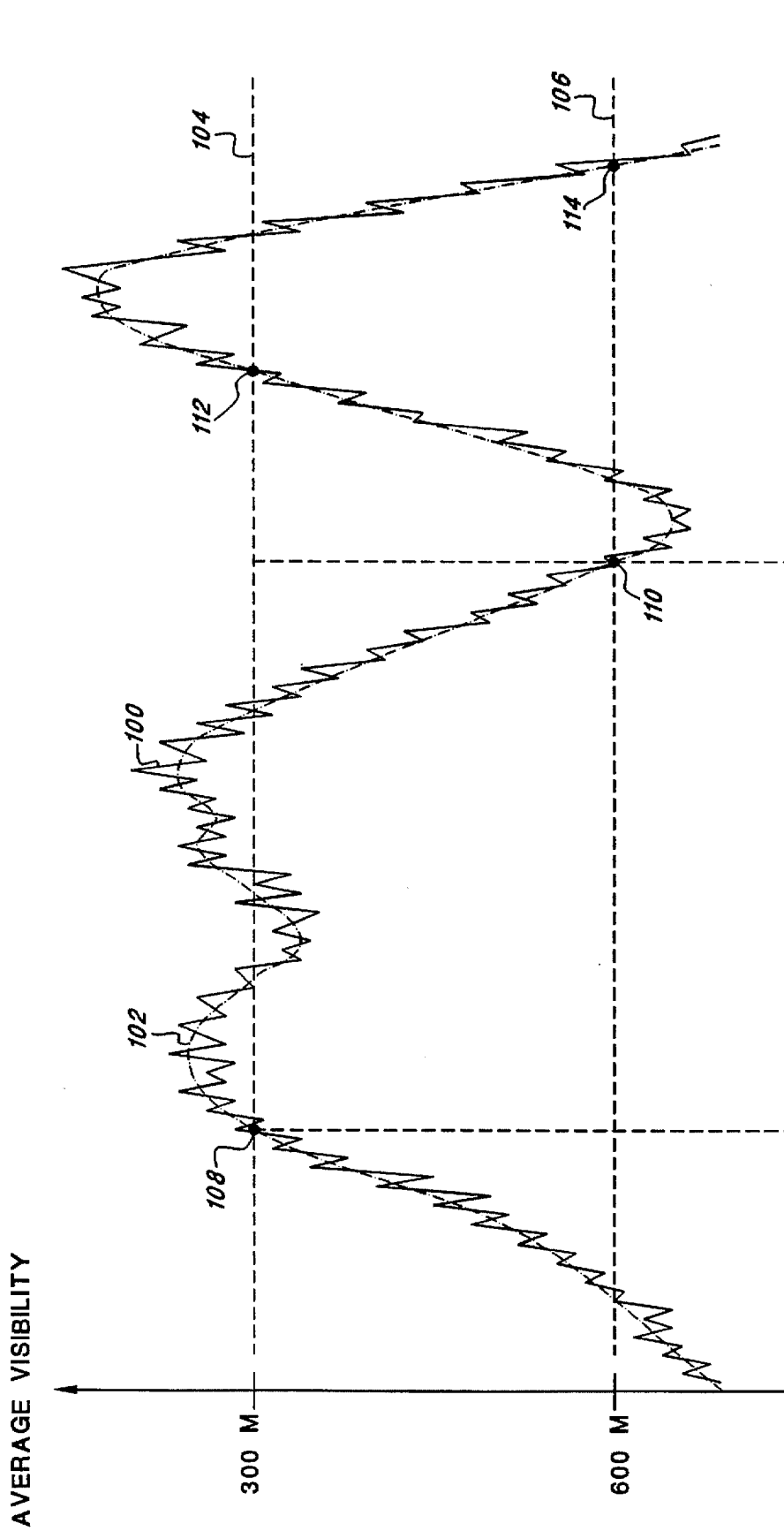
FIG. 2 is an exemplary graph showing instantaneous visibility and a ten-sample running average visibility, such as might be detected by the backscatter-type visibility detector of FIG. 1, over time.

Referring next to FIG. 2, an exemplary graph is shown illustrating instantaneous visibility, i.e., the backscatter signal samples, and a backscatter ten-sample running average signal, such as might be detected by the backscatter-type visibility detection system 10 of the above-described embodiment. Time is shown along an abscissa axis (or x-axis) and average visibility is shown along an ordinate axis (or y-axis). The ordinate axis is shown with more negative amounts of visibility nearer to the top of the page as oriented in FIG. 2. Time is shown on the abscissa axis increasing to the right, as oriented in FIG. 2. A solid line 100 in the graph represents the backscatter signal samples taken over time. As can also be seen, the samples are represented using a continuous curve, however, it will be understood by one skilled in the art that such samples are discreet values taken at discreet times, here shown as a continuous curve for illustration purposes only.

As can be seen, the curve representing the samples is rather "jagged", indicating the rather sharp localized variations that can occur between successive samples as a result of clear areas passing over the backscatter receiver or billowing. A dotted dashed line 102 represents the backscatter ten-sample running average, and illustrates the smoothing effect such average has on the backscatter samples. As a result of such smoothing, the large localized variations in the backscatter samples (due to clear areas or billowing) are largely eliminated, presenting a more accurate representation of the actual visibility conditions near the backscatter type visibility detection system 10. Also shown as a first horizontal dashed line 104 is the upper threshold, i.e., the threshold at which the alarm signal is activated by the hysteresis threshold detector 54a. A second horizontal dashed line 106 represents the lower threshold at which the hysteresis threshold detector 54a turns off the alarm signal. As illustrated, the alarm signal will be turned on at a first point 108, at which the backscatter ten-sample running average crosses the upper threshold 104 as the ten-sample running average 102 signals a decreasing visibility, i.e., backscatter increases.

Subsequent to this crossing of the upper threshold 104, the backscatter ten-sample running average 102 again crosses the upper threshold 104 as visibility momentarily increases, i.e., backscatter decreases. The alarm signal continues to be generated even after the backscatter ten-sample running average 102 has again crossed the upper threshold 104. Subsequent to this second crossing of the upper threshold, the backscatter ten-sample running average again indicates that the visibility near the backscatter-type visibility detection system 10 is decreasing and the backscatter ten-sample running average 102 crosses the upper threshold 104 a third time. The alarm signal continues to be generated from the time the backscatter ten-sample running average first crosses the upper threshold (at the point 108) through when it dips below the upper threshold 104 and again goes above the upper threshold 104. As shown, the backscatter ten-sample running average 102 then again dips below the upper threshold 104, and the alarm signal continues to be maintained by the hysteresis threshold detector 54a.

In accordance with the present embodiment, when the backscatter ten-sample running average finally goes below the lower threshold 106 (at a point 110), the hysteresis threshold detector 54a stops generating the alarm signal. As shown, shortly after the backscatter ten-sample running average 102 dips below the lower threshold 106, it again rises above the lower threshold 106 and continues to go up, signaling another decrease in visibility. As it rises above the lower threshold 106, the alarm signal is not generated, but once it reaches the upper threshold 104 (at a point 112), the alarm signal is again generated. Finally, visibility again increases causing the backscatter ten-sample running average 102 to drop below the upper threshold 104. When the backscatter ten-sample running average 102 dips below the lower threshold 106 (at a point 114), the alarm signal again ceases to be generated.

In this way, one skilled in the art will recognize, the present invention creates a hysteresis in the generation of and stopping of generation of the alarm signal, so as to avoid the effects of small pockets of clear atmosphere, or small pockets of low visibility atmosphere, that may momentarily pass in front of the transmitter 16 and backscatter receiver 26. To further minimize the effects of these "billows" of airborne visibility impeding agents 20, the backscatter ten-sample running average 102 is utilized to smooth out localized variations in the backscatter signal samples 106.

Figure 3:
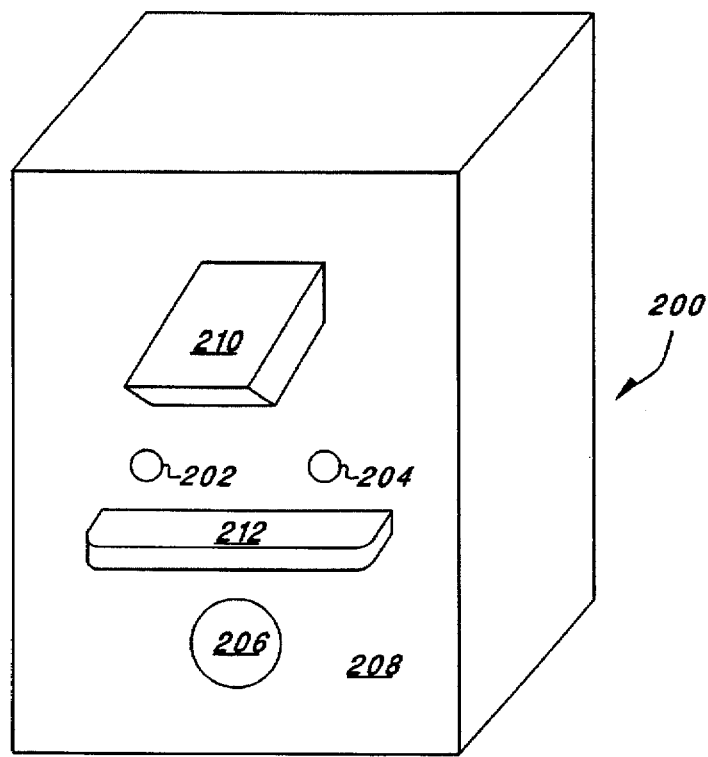
FIG. 3 is an exterior isometric view of one embodiment of a housing in which a backscatter-type visibility detector, such as the embodiment of FIG. 1, can be housed.

Referring next to FIG. 3, an exterior isometric view is shown of one embodiment of a housing 200 in which the backscatter-type visibility detection system of the present embodiment can be housed. The housing 200 includes three openings 202, 204, 206 on a front surface 208. Through the first and second of these openings 202, 204 infrared radiation from the transmitter is emitted. The transmitter, in one embodiment, comprises a pair of lenses that cover the first and second openings and a pair of infrared light emitting diodes, such as Part No. OD 663 available from Opto Diode Corporation of Newbury Park, Calif. The light emitting diodes are located behind the lenses. The third opening 206 allows backscattered infrared radiation to return through, a lens positioned in the third opening, and an infrared detector, such as Pat. No. OSI 1193A available from Opto Sensors, Inc. of Torrance, Calif.

Above the first and second openings 202, 204 a rectangular arm 210 angled slightly downward protrudes from the front surface 208 of the housing 200. Behind an opening on the underside of this rectangular arm (hidden from the field view of FIG. 3) is the reference receiver, which may consist of yet another lens positioned in an opening in the arm 210 and an infrared detector similar to that used for the backscatter detector. Infrared radiation (or light) emitted from the transmitter 16 through the first and second openings 202, 204 impinges directly upon the reference receiver 38 on the hidden underside of this rectangular arm 210.

One important feature of the present embodiment illustrated in FIG. 3 is a meniscus barrier 212 in the form of a horizontally oriented ridge that protrudes from the front surface 208 and is interposed between the first and second openings 202, 204, and the third opening 206. The meniscus barrier 212 prevents the formation of a continuous meniscus of water vapor, such as is commonly a result of fog, from accumulating on the front surface 208 between the first and second openings 202, 204, and the third opening 206. As described above, if this meniscus of water vapor were allowed to form between the first and second openings 202, 204, and the third opening 206, it could diffuse light emitted from the transmitter 16 by reflecting the infrared light off of the interior surface of the meniscus until it is carried through the third opening 206 to the backscatter receiver 26. The backscatter receiver 26 interprets this diffused light as backscattered light, and therefore bases its determination of the amount of infrared light backscatter on, in part, this diffused light. As a result, backscatter-type visibility detection systems heretofore known were prone to signal the presence of low visibility when in fact visibility was relatively high. This erroneous signaling of low visibility was often due, in part, to the diffusion of infrared light through the fluid meniscus across the surface of the housing of the backscatter-type visibility detection system. Thus, the present embodiment eliminates the effects of meniscus diffusion, and therefore overcomes this significant problem present in the prior art.

Figure 4:
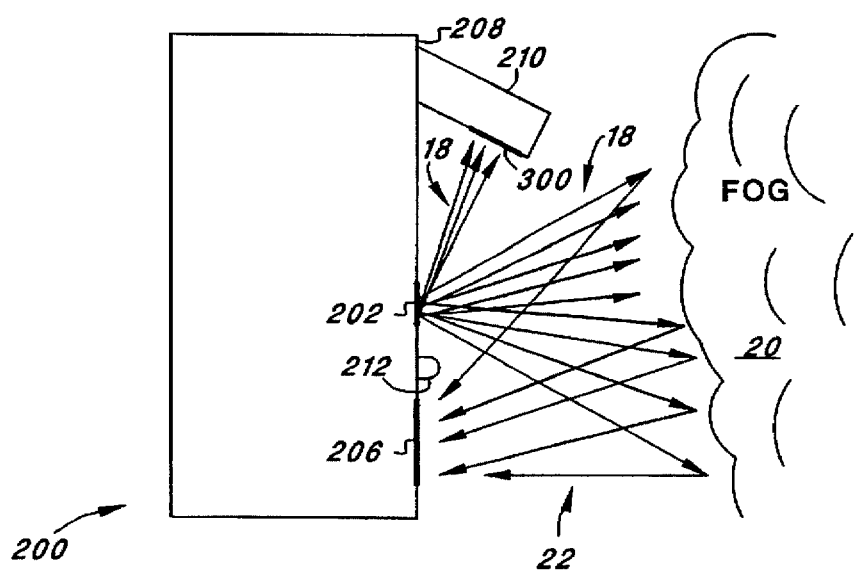
FIG. 4 is an exterior side view of the one embodiment of the housing shown in FIG. 3.

Referring next to FIG. 4, an exterior side view is shown of the one embodiment of the housing 200. The first opening 202 is shown (represented by a darkened area of the right most surface of the housing 200 depicted in FIG. 4). The third opening 206 is shown (similarly depicted), and the rectangular arm 210 is shown, with an opening 300 for the reference receiver 38 represented by a darkened area below and to the left on the rectangular arm 300. The meniscus barrier 212 is further represented interposed between the first opening 202 and the third opening 206. The second opening is not shown in FIG. 4. Emitted from the transmitter 16 located, in part, behind the first opening 202, is the infrared radiation 18 (or light). Some of the infrared radiation 18 impinges directly upon the reference receiver 38 located behind the opening (or window) in the rectangular arm 210. The rest of the infrared light 18 is emitted into the atmosphere beyond the first window 202. As shown in FIG. 4, fog 20 is present in the atmosphere, and some of the infrared radiation 22 incident on the fog 20 is reflected back to the backscatter-type visibility detection system 10. A portion of the backscattered infrared radiation 22 enters the housing 200 through the third opening 206 and impinges upon the backscatter receiver 26. As described above, the backscatter receiver 26 generates a backscatter signal indicative of the amount of infrared radiation backscatter by the fog 20 or other airborne visibility impeding agent.

Figure 5:
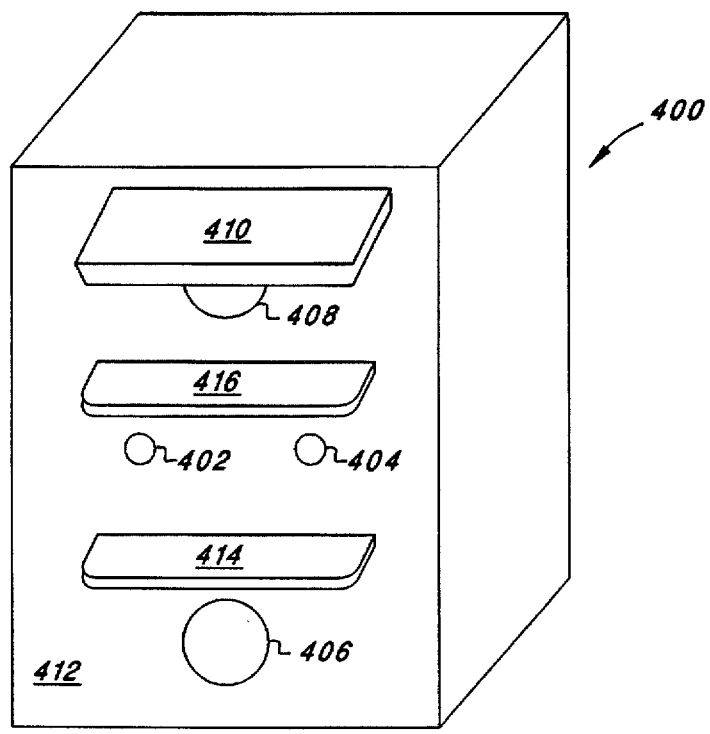
FIG. 5 is an exterior isometric view of another embodiment of a housing in which a backscatter-type visibility detector, such as the embodiment of FIG. 1, can be housed.

Referring next to FIG. 5, an exterior isometric view is shown of another embodiment of a housing 400 in which the backscatter-type visibility detection system 10 of the present embodiment can be housed. First, second, third and fourth openings 402, 404, 406, 408 are shown in the housing 400. As with the above described embodiment of the housing 400, the first and second openings 402, 404 permit the infrared radiation 18 emitted from the infrared light emitting diodes of the transmitter 16 to pass through the housing 400 and into the atmosphere near the backscatter-type visibility detection system 10. Also, as with the above-described embodiment of the housing, the third opening 406 allows backscattered infrared radiation 22 to enter the backscatter receiver 26. The fourth opening 408 of the housing 400 allows infrared radiation 18 to enter the reference receiver after it is reflected back toward the housing by a reflector 410 that protrudes from the front surface 412 of the housing 400. The reflector 410 also serves to block any backscattered radiation 22 from entering the fourth opening 408. As with the above-described embodiment of the housing, the meniscus barrier 414 is used between the first and second openings 402, 404, and the third opening 406. Another meniscus barrier 416 is used between the first and second openings 402, 404 and the fourth opening 408.

Figure 6:
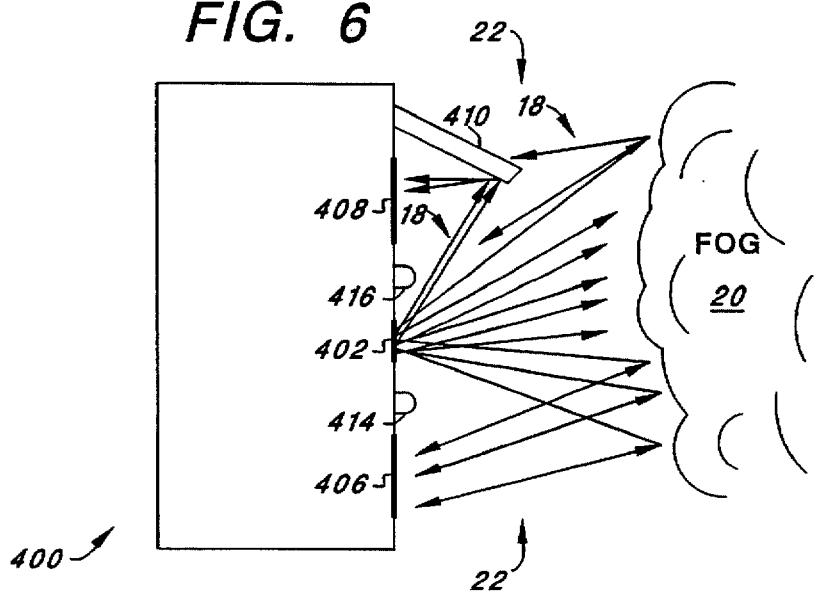
FIG. 6 is an exterior side view of the other embodiment of the housing shown in FIG. 5.

Referring first to FIG. 6, an exterior side view is shown of the other embodiment of the housing 400.

The first, third and fourth openings 402, 406, 408 are shown, as are the meniscus barriers 414, 416 and the reflector 410. As can be seen, infrared light 18 emitted from the first opening 402 impinges on both the underside of the reflector 410 and on, e.g., fog 20 in the atmosphere near the backscatter-type visibility detection system 10. The infrared light 18 reflected off of the reflector 410, which may be, e.g., a mirror, is directed toward the fourth opening 408 and into the reference receiver 38. Infrared radiation 22 backscattered by the fog 20 is reflected back toward the third opening 406 and impinges upon the backscatter receiver 26. Any infrared radiation 22 backscattered toward the fourth opening 408 hits the back of the reflector 410 so that it is not detected by the reference detector 38.

Referring to FIGS. 7, 8, 9, 10, 11A, 11B, 11C and 11D together, a detailed schematic diagram is shown of one implementation of the present embodiment of the backscatter-type visibility detection system.

Figure 7:
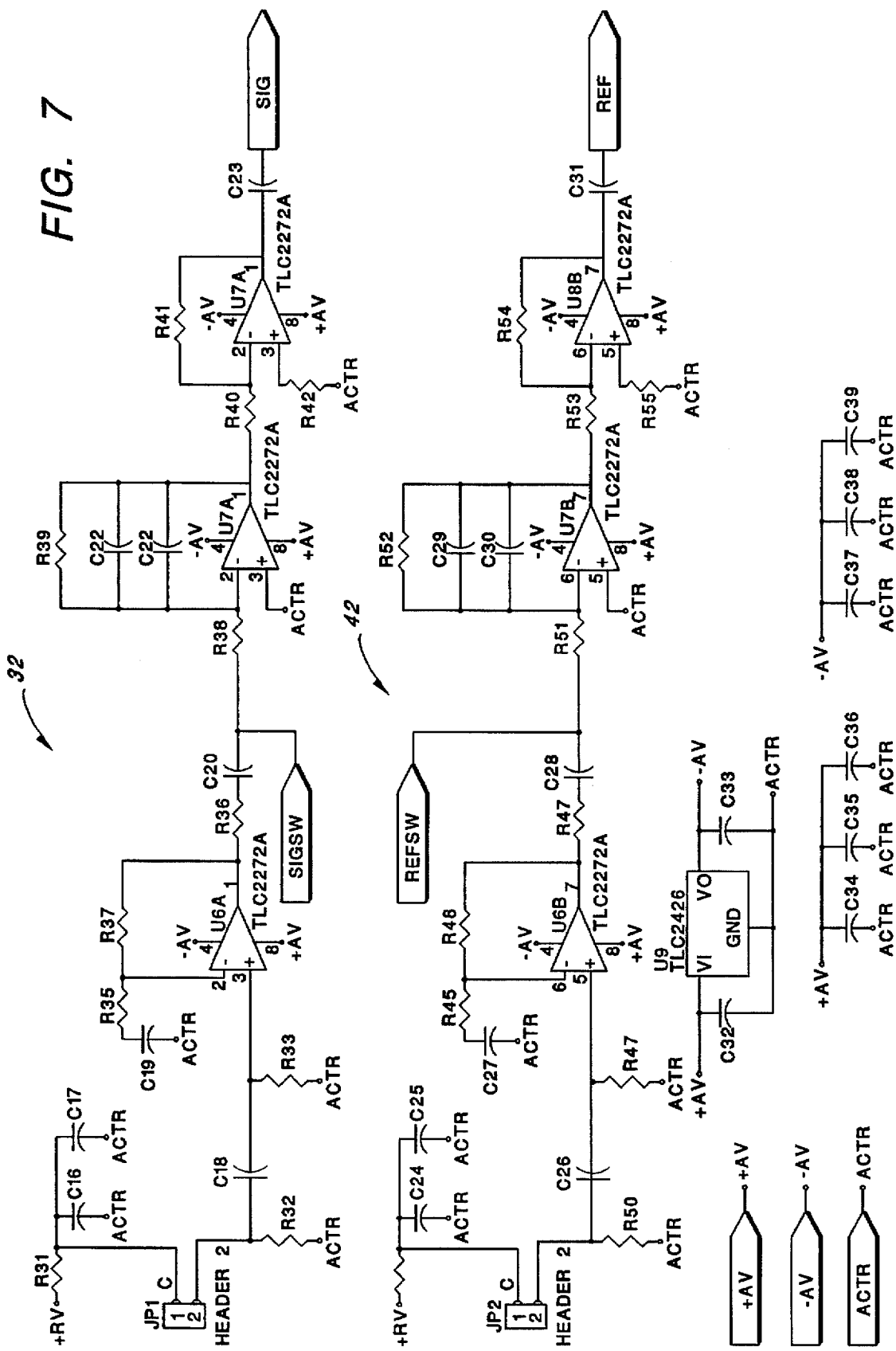
FIGS. 7, 8, 9, 10, 11A, 11B, 11C and 11D together are a detailed schematic diagram showing of one implementation of the embodiment of a backscatter-type visibility detector of FIG. 1.

FIG. 7 shows a first analog portion of the implementation. Specifically, the amplifier 32 (that is coupled to the backscatter receiver 26), and the amplifier 42 (that is coupled to the reference receiver 38) are shown. As with each of FIGS. 7, 8, 9, 10, 11A, 11B, 11C and 11D, FIG. 7 should be self-explanatory to one skilled in the art and therefore further explanation is not provided.

Figure 8:
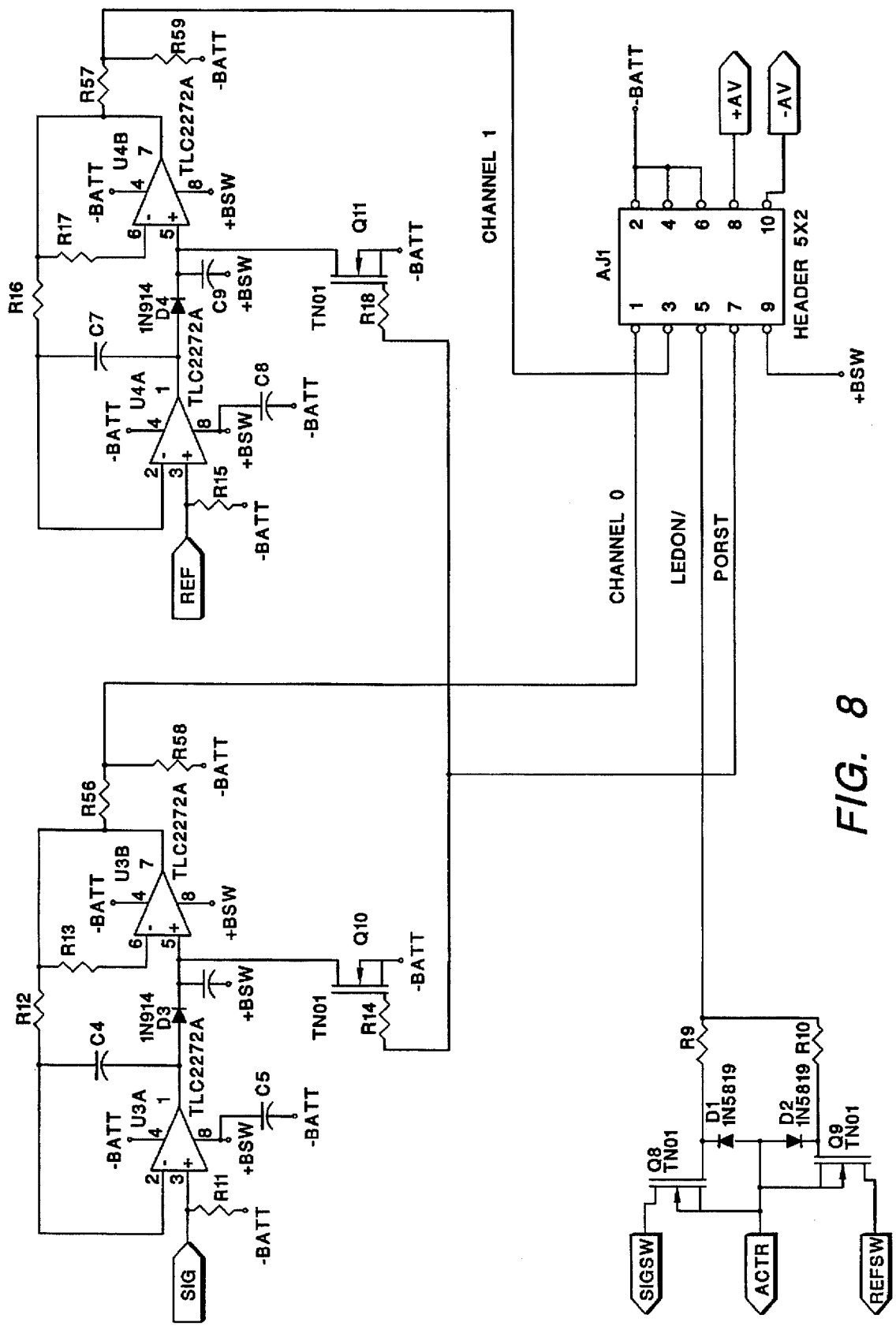
Figure 9:
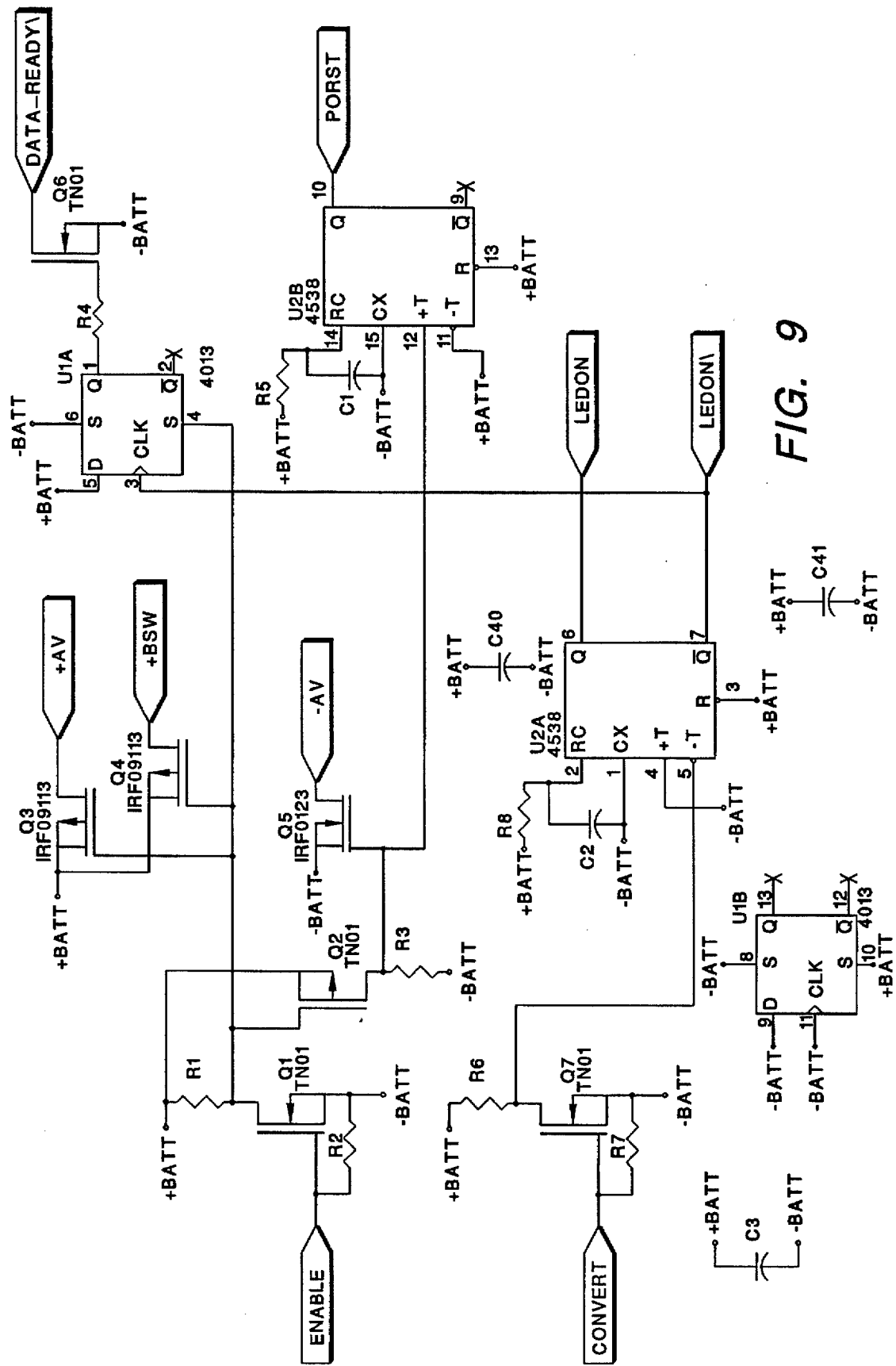
Figure 10:
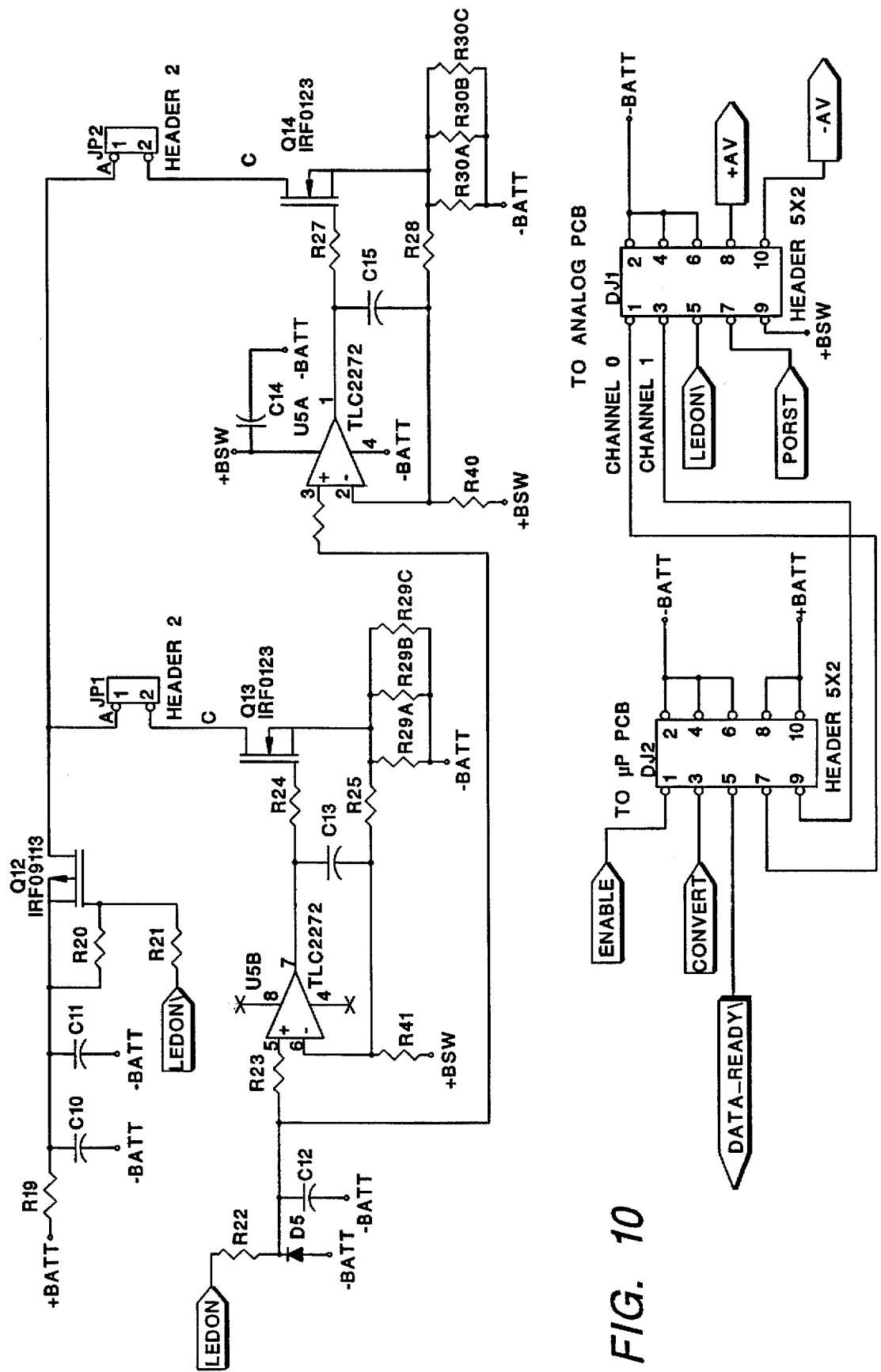
Figure 11A:
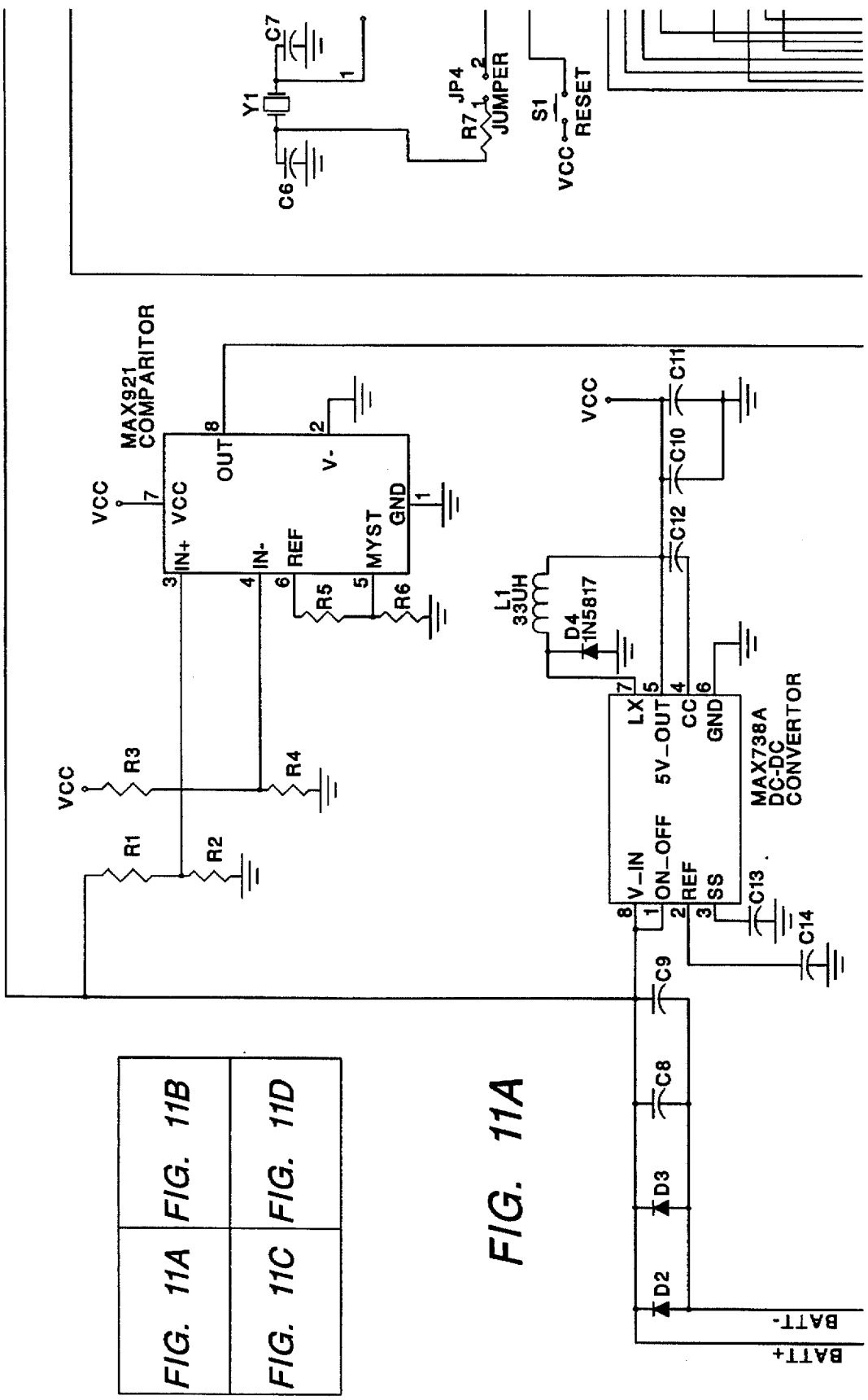
Figure 11B:
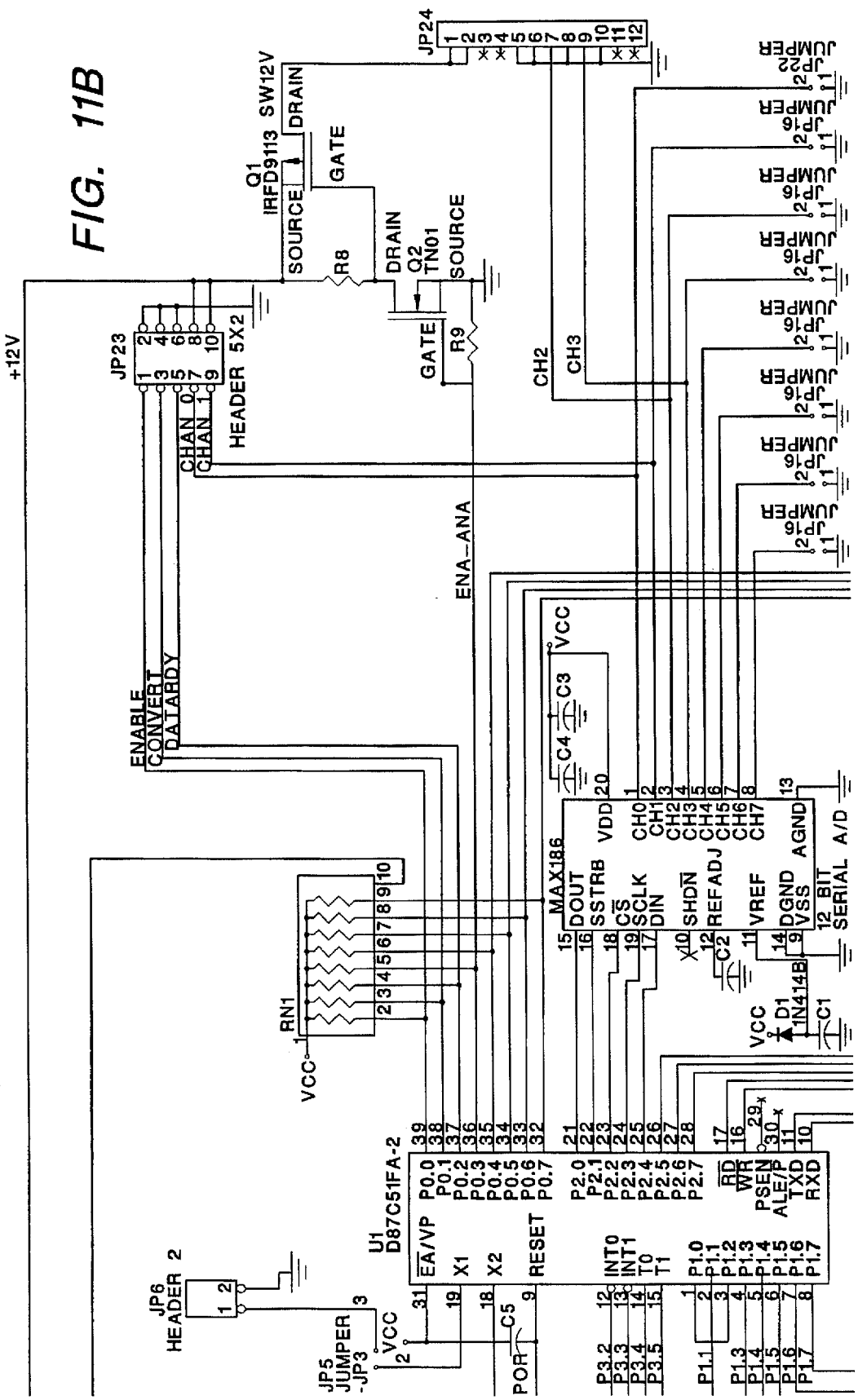
Figure 11C:
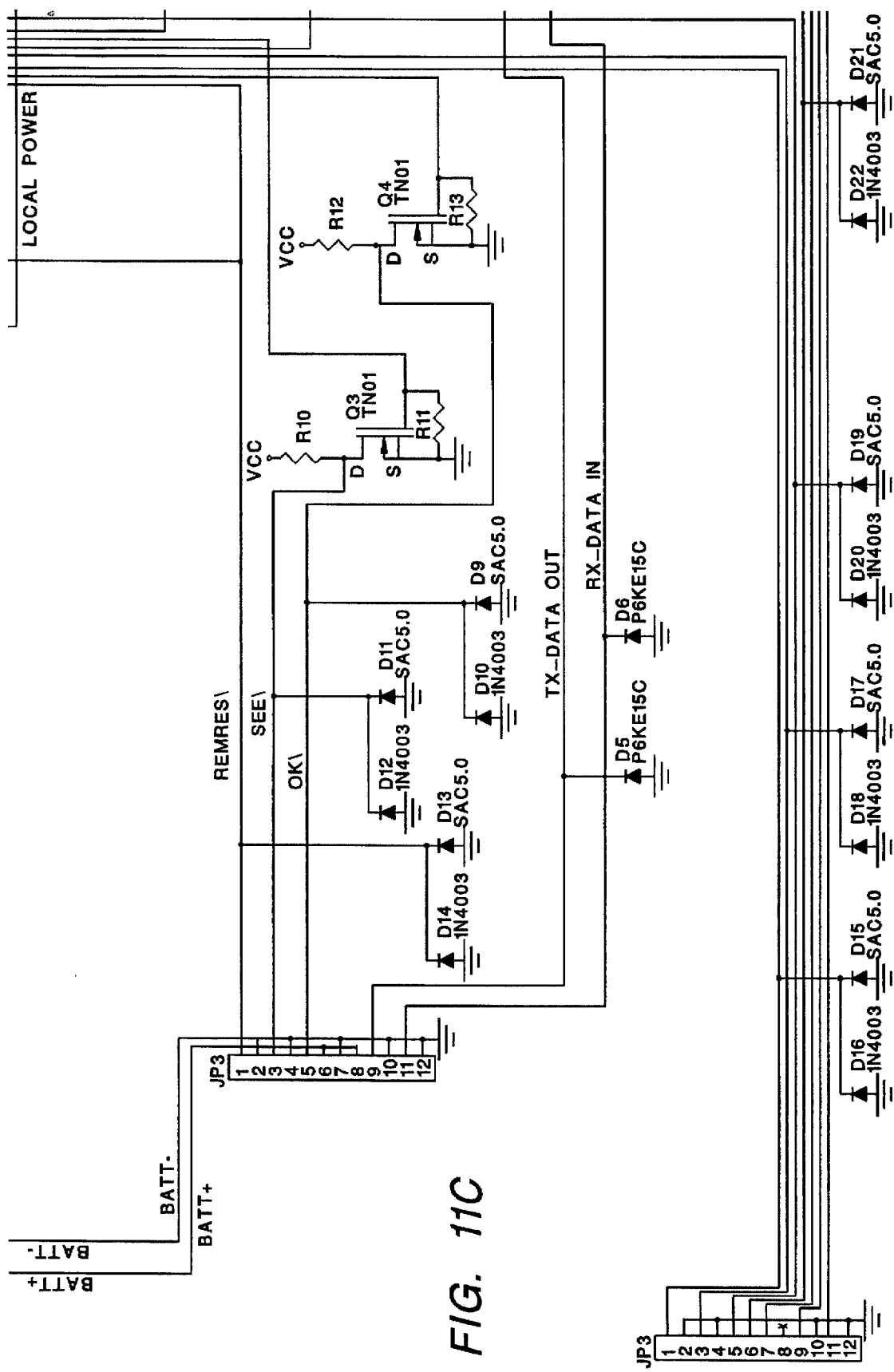
Figure 11D:
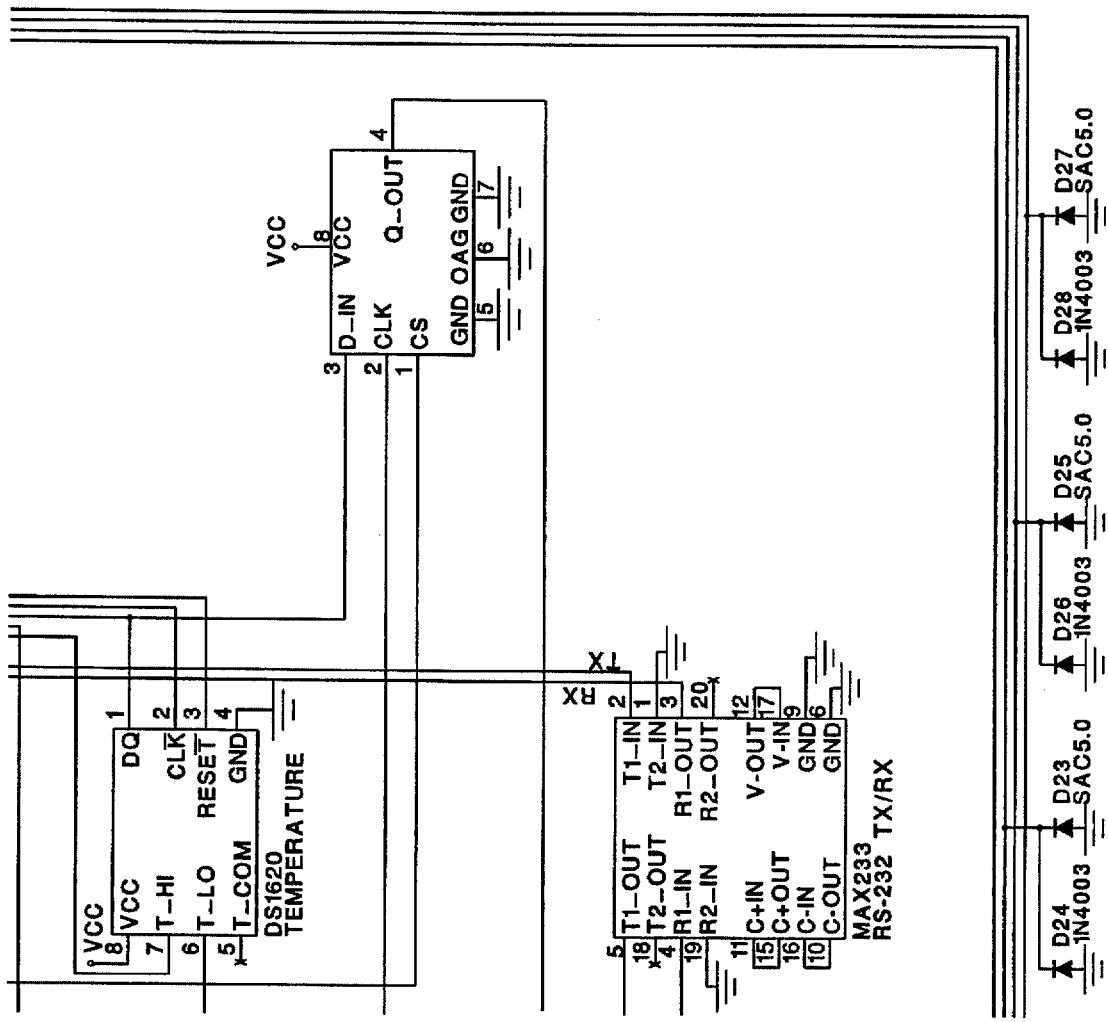
Figure 12:
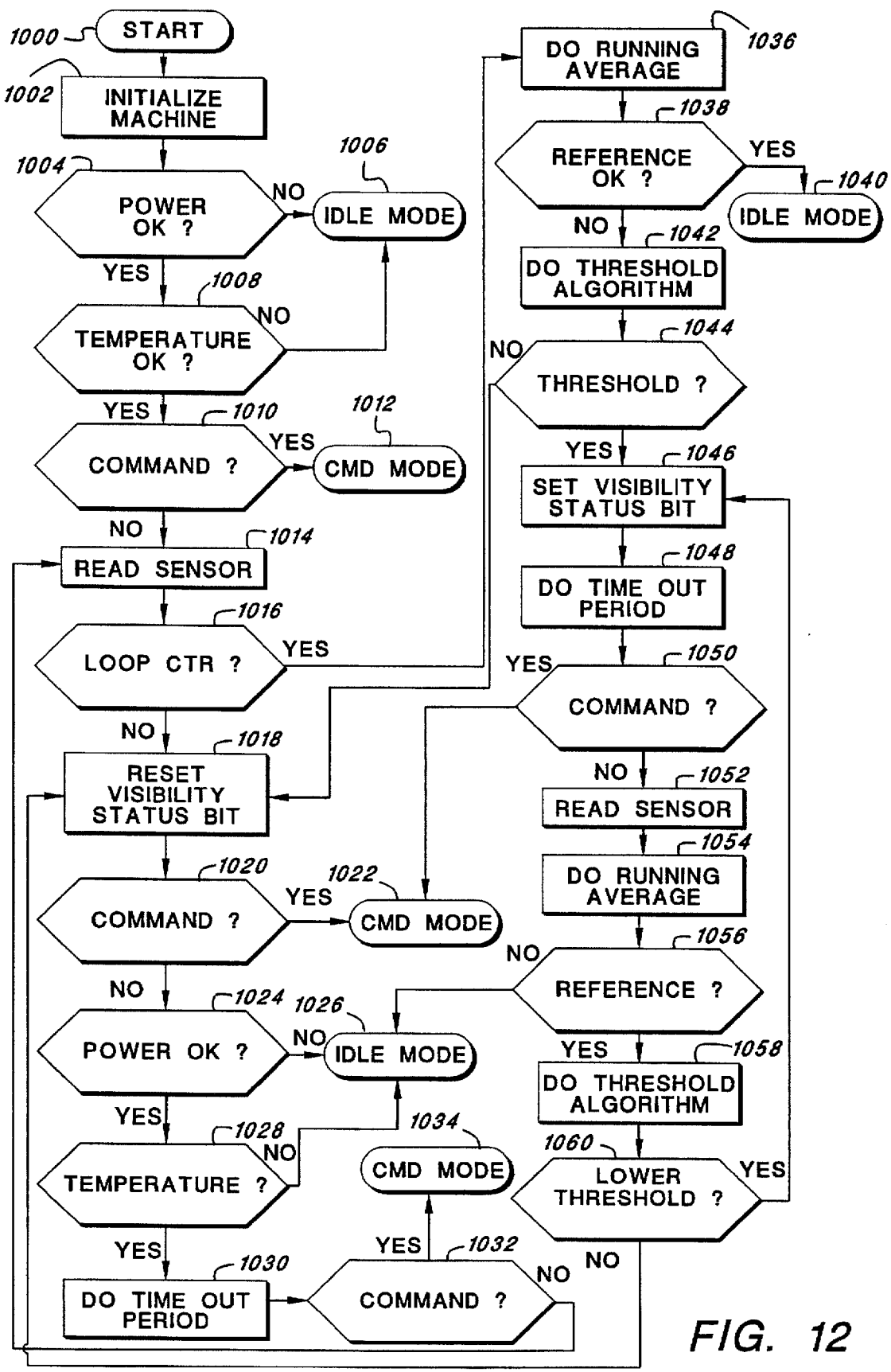
FIG. 12 is a flow chart showing the steps traversed by the implementation of FIGS. 7, 8, 9, 10, 11A, 11B, 11C and 11D when operated.

FIG. 8 shows a second analog portion of the present implementation. In FIGS. 9 and 10, first and second digital portions of the present implementation are shown, and in FIGS. 11A, 11B, 11C and 11D, a microprocessor section of the implementation is illustrated.

Referring next to FIG.. 12, a flow chart is shown illustrating the steps traversed by the present embodiment. Upon being powered up (Block 1000), the present embodiment is initialized (Block 1002) and a power monitor circuit, such as is known in the art, determines (Block 1004) whether the power supplied to the backscatter-type visibility detection system is sufficient. If such power is not sufficient, e.g., is of a voltage that is too low, then the backscatter-type visibility detection system enters (Block, 1006) an idle mode where it remains until it is reset, or until the power is restored to an appropriate operating level. In the event that the power is adequate for operation of the backscatter-type visibility detection system, a temperature-checking circuit determines (Block, 1008) whether the temperature within the housing of the backscatter-type visibility detection system is within safe operating parameters for the system. If the temperature is not within safe operating parameters, the backscatter-type visibility detection center enters the idle mode until the system is either reset or until the temperature falls within the safe operating range.

In the event the temperature is within the safe operating range, the backscatter-type visibility detection system determines (Block 1010) whether a command has been sent to the system through, e.g., a serial communications interface. In the event a command has been sent to the system through the communications interface, the system enters (Block 1012) a command mode, wherein it accepts commands from an external programmer, such as a personal computer or notebook computer, allowing an operator of the external programmer to manually set the thresholds, and other operating parameters for the backscatter-type visibility detection system.

In the event no command has been sent through the communications interface to the backscatter-type visibility detection system, the periodic signal is generated by a clock circuit, causing the generation of a pulse of infrared light and the detection (Block 1014) of any infrared light impinging on the backscatter receiver and any infrared light impinging on the reference receiver. Preferably, the infrared light from the transmitter is generated for a period of time prior to the activation of the backscatter receiver and the reference receiver so that the infrared emitters of the transmitter can reach a steady operating state before the amount of backscattered infrared radiation, and the amount of reference infrared radiation are measured (Block 1014).

Once the backscatter receiver and the reference receiver are read in this manner, the determination (Block 1016) is made as to whether a loop counter has reached a count of ten. If the loop counter has not reached the count of ten, the visibility status bit is reset (Block 1018) (signifying that visibility is high), and a determination (Block 1020) is made as to whether a command has been received from the external programmer.

In the event a command has been received from the external programmer, command mode is entered (Block 1022) and if a determination is made that no command has been received from the external programmer, the power monitoring circuit detects (Block, 1024) the condition of the power, and enters (Block 1026) idle mode in the event the power is inadequate to operate the backscatter-type visibility detection system. If the power is adequate to operate the backscatter-type visibility detection system, then the temperature monitoring circuit determines (Block 1028) whether the temperature is within a safe operating range. In the event the temperature is not within the safe operating range, the backscatter-type visibility detection system enters (Block 1026) the idle mode as described above.

If, however, the temperature is within a safe operating range, then a time delay is initiated (Block 1030) for, e.g., 30 seconds and another check is made (Block 1032) as to whether a command has been received from the external programmer. In the event that a command is received, the backscatter-type visibility detection system enters the command mode (Block 1034), and if a command is not received, the periodic signal is generated and the backscatter receiver and reference receiver are read (Block, 1014) after the transmitter transmits a pulse of infrared radiation.

Execution continues with the determination (Block 1016) as to whether the loop counter has reached the count of ten, and the steps described above (Blocks 1020, 1022, 1024, 1026, 1028, 1030, 1032 and 1034) following such determinations are repeated until a determination is made that the loop counter has reached the count of ten. Each time the loop counter is checked it is incremented by one count.

When the loop counter reaches the count of ten, the readings from the backscatter receiver and reference receiver are averaged (Block, 1036) over the ten program loops described above. If the average of the reference samples generated in response to the reference receiver is below a prescribed threshold (Block, 1038), indicating that only a small amount or no infrared radiation is impinging on the reference receiver, the backscatter-type visibility detection system enters (Block, 1040) the idle mode until the system is reset or until the average of the reference samples exceeds the prescribed threshold. In the event, however, the running average of the reference samples exceeds the prescribed threshold, as will normally be the case, a threshold algorithm is computed (Block, 1042). The threshold algorithm is as follows:

(Scaled Backscatter Ten-Sample Running Average) =

(Backscatter Ten-Sample Running Average) × $\left[ \frac{\text{(Baseline Determined During Calibration)}}{\text{(Reference Ten-Sample Running Average)}} \right]$ Note that the threshold algorithm incorporates both the backscatter ten-sample running average and the reference ten-sample running average. As each of these averages can be assumed to be equally affected by temperature, contaminants on the lenses of the backscatter detector and reference detector, and the like, these effects are eliminated by the threshold algorithm when the backscatter ten-sample running average is divided by the reference ten-sample running average.

Following execution of the threshold algorithm, a determination is made (Block 1044) as to whether the upper threshold is exceeded by the scaled backscatter ten-sample running average determined by the threshold algorithm. If the upper threshold is not exceeded, then the visibility status bit is reset (Block 1018) and execution continues (Blocks 1020 et seq.) as described above. If however, the upper threshold is exceeded, the visibility status bit is set (Block 1046) and another delay period is initiated (Block 1048). Following this other delay period, a determination is made (Block 1050) as to whether or not a command has been received from the external programmer, and if a command has been received, the backscatter-type visibility detection system enters (Block, 1022) the command mode.

In the event, however, a command has not been received, the periodic signal is generated causing the transmitter to generate a pulse of infrared light and causing the backscatter receiver and reference receiver to generate the backscatter signal and reference signal respectively (Block, 1052). Following the generation (Block, 1052) of the backscatter signal and the reference signal, a ten-sample running average indicative of the backscatter signal over the last ten sensor readings and a ten-sample running average indicative of the reference signal over the last ten sensor readings is determined (Block, 1054).

Next, a determination is made (Block, 1056) as to whether the reference ten-sample running average exceeds a reference threshold, and if it does not, the backscatter-type visibility detection system enters the idle mode (Block, 1026). However, in the event the backscatter-type visibility detection system determines that the reference ten-sample running average does exceed the reference threshold, then the threshold algorithm, described above, is recomputed (Block, 1058). In the event the scaled backscatter ten-sample running average determined by the threshold algorithm is less than the lower threshold (Block, 1060), then the visibility status bit is reset (Block 1018) and execution continues (Block 1020 et seq.) as described above. If however the threshold algorithm determines (Block 1060) that the scaled backscatter ten-sample running average continues to exceed the lower threshold, the visibility status bit is set (Block, 1046) and execution continues (Blocks 1040 et seq.) as described above.

In this way, the present embodiment utilizes the backscatter ten-sample running average and the reference ten-sample running average as inputs to the threshold algorithm in order to compute the scaled backscatter running average. The scaled backscatter running average is then compared to either the lower threshold or the upper threshold depending on whether the visibility status bit is currently set or reset. The present embodiment also continuously monitors the reference ten-sample running average to insure that it exceeds the reference threshold and enters the idle mode (when it generates a NOT OK status bit) in the event the reference ten-sample running average falls below the reference threshold. The system remains in the idle mode until such time as the backscatter-type visibility detection system is reset or the reference ten-sample running average again exceeds the reference threshold.

The above described steps also implement one embodiment of the hysteresis threshold detector (FIG. 1) by comparing the scaled backscattered ten-sample running average to an upper threshold so long as visibility is adequate, i.e., high. Once the scaled backscattered ten-sample running average exceeds the upper threshold, the visibility status bit is set, indicating that low visibility condition exists. After the visibility status bit is set, the scaled backscattered ten-sample running average is repeatedly compared to the lower threshold until such time as the scaled backscattered ten-sample running average falls below the lower threshold, causing the visibility status bit to be reset. Once the visibility status bit is reset, the scaled backscattered ten-sample running average is again repeatedly compared with the upper threshold until the visibility status bit is again set in response to the scaled backscattered ten-sample running average exceeding the upper threshold. In this way, the present embodiment is made relatively immune from the effects of billowing (i.e., pockets of clear atmosphere or pockets of atmosphere that are more densely occupied by airborne visibility impeding agents), which in prior art systems tend to cause relatively large localized variations in the detected amount of backscattered infrared radiation. This problem is further addressed by using the two ten-sample running averages to smooth out anomalous sudden changes in the detected amount of backscatter.

While the invention herein disclosed has been described by means of specific embodiments and applications thereof, numerous modifications and variations could be made thereto by those skilled in the art without departing from the scope of the invention set forth in the claims.

What is claimed is:

1. A system for detecting an airborne visibility impeding agent comprising:

an infrared emitter positioned for emitting infrared radiation;

an infrared backscatter detector positioned to receive a first portion of the infrared radiation having been backscattered by the airborne visibility impeding agent, the infrared backscatter generating a backscatter signal in response to a detected amount of the first portion of infrared radiation;

an infrared reference detector positioned to receive a second portion of the infrared radiation not having been backscattered by the airborne visibility impeding agent, the infrared reference detector generating a reference signal in response to a detected amount of the second portion of infrared radiation; and a visibility determination circuit coupled to the infrared emitter, the infrared backscatter detector and the infrared reference detector, for averaging the reference signal and the backscatter signal over time, for scaling the backscatter signal having been averaged using the reference signal having been averaged, for determining a determined amount of the infrared radiation backscattered by the airborne visibility impeding agent as a function of the backscatter signal having been averaged and scaled, for determining whether the determined amount exceeds a prescribed threshold, and for commencing generating of an alarm signal in event the determined amount is determined to exceed the prescribed threshold.

2. The system of claim 1 wherein said visibility determination circuit includes means for determining whether said determined amount is less than a lower threshold, and for terminating said generating of said alarm signal in the event said determined amount is determined to be less than the lower threshold.

3. A system for detecting an airborne visibility impeding agent comprising:

a housing having a surface;

an infrared emitter positioned in the surface, for emitting infrared radiation;

an infrared backscatter detector positioned in the surface to receive a portion of the infrared radiation having been backscattered by the airborne visibility impeding agent;

a meniscus barrier including a ridge, on the surface, interposed between the infrared emitter and the infrared backscatter detector, for preventing diffusion of the infrared radiation through a fluid meniscus on the surface between the infrared emitter and the infrared backscatter detector;

a visibility determination circuit coupled to the infrared emitter and the infrared backscatter detector, for determining an amount of the infrared radiation backscattered by the airborne visibility impeding agent, for determining whether the amount determined exceeds a prescribed threshold, and for generating an alarm signal in event the amount is determined to exceed the prescribed threshold.

4. The system of claim 3 wherein said visibility determination circuit includes means for determining said amount of said infrared radiation backscattered by said airborne visibility impeding agent by averaging said portion of the infrared radiation having been backscattered that is received over time.

5. The system of claim 4 wherein said visibility determination circuit includes means for determining whether said amount is less than a lower threshold, and for terminating said generating of said alarm signal in the event said amount is determined to be less than the lower threshold.

6. The system of claim 4 including:
   an infrared reference detector positioned to receive another portion of said infrared radiation not having been backscattered by said airborne visibility impeding agent;
   wherein said visibility determination circuit includes means for determining said amount of said infrared radiation backscattered by said airborne visibility impeding agent by averaging said other portion of the infrared radiation not having been backscattered that is received over time, and by scaling said portion of said infrared radiation having been backscattered, having been averaged over time, said means for determining said determined amount using said other portion of said infrared radiation not having been backscattered, having been averaged over time, in said scaling of said portion of said infrared radiation, having been backscattered, and having been averaged over time.

7. The system of claim 3 wherein said infrared emitter includes means for emitting infrared radiation having an intensity of at least 2 watts and a wavelength of 880 nm.

8. The system of claim 3 including:
   a timing circuit coupled to said infrared emitter, and said infrared backscatter detector, for periodically activating said infrared emitter, and said infrared backscatter detector.

9. A method for detecting an airborne visibility impeding agent comprising:
   emitting infrared radiation away from an infrared emitter;
   detecting an amount of a first portion of the infrared radiation having been backscattered by the airborne visibility impeding agent;
   generating a backscatter signal in response to the amount of the first portion detected;
   detecting an amount of a second portion of the infrared radiation not having been backscattered by the airborne visibility impeding agent;
   generating a reference signal in response to the amount of the second portion detected;
   determining an actual amount of the infrared radiation backscattered by the airborne visibility impeding agent in response to the backscatter signal and the reference signal including averaging the backscatter signal over time, averaging the reference signal over time, and scaling the backscatter signal having been averaged using the reference signal having been averaged;
   determining whether the actual amount exceeds a prescribed threshold; and
   generating an alarm signal in event the actual amount is determined to exceed the prescribed threshold.

10. The method of claim 9 including:
    determining whether said actual amount is less than a lower threshold; and
    terminating said generating of said alarm signal in the event said actual amount is determined to be less than the lower threshold.

11. A method for detecting an airborne visibility impeding agent comprising:
    calibrating including:
      generating a recalibrate signal;
      emitting, in response to the recalibrate signal, infrared radiation away from an infrared emitter;
      detecting a baseline amount of the infrared radiation having been backscattered; and
      generating a calibration signal in response to the baseline amount of the infrared radiation detected; and then
    determining a prescribed threshold as a function of the calibration signal; and then
    detecting reduced visibility including:
      emitting infrared radiation away from the infrared emitter;
      detecting a detected amount of the infrared radiation having been backscattered by the airborne visibility impeding agent;
      generating a detection signal in response to the detected amount of the infrared radiation including averaging the reference amount over time;
      detecting a reference amount of said infrared radiation not having been backscattered by said airborne visibility impeding agent;
      generating a reference signal in response to the reference amount including averaging the reference amount over time;
      determining a determined amount of the infrared radiation backscattered by the airborne visibility impeding agent by scaling the detection signal using the reference signal;
      determining whether the determined amount exceeds the prescribed threshold; and
      generating an alarm signal in event the determined amount is determined to exceed the prescribed threshold.

12. The method of claim 11 including:
    detecting increased visibility including:
      determining a lower threshold as a function of said calibration signal;
      determining whether said detection signal is less than the lower threshold; and
      terminating said generating of said alarm signal in the event said detection signal is determined to be less than the lower threshold.

13. The method of claim 11 including:
    detecting a fault condition, including:
      determining whether said reference amount is less than a reference threshold; and
      generating a fault signal, indicating the fault condition, in event said reference amount is determined to be below the reference threshold.

14. A method for detecting an airborne visibility impeding agent comprising:
    detecting a reduced visibility condition including:
      emitting infrared radiation away from an infrared emitter;
      detecting a first amount of the infrared radiation emitted during the first period of time having been backscattered by the airborne visibility impeding agent;
      generating a first detection signal in response to the first amount of the infrared radiation including averaging the first amount over time;
      detecting a first reference amount of said infrared radiation not having been backscattered by said airborne visibility impeding agent;
      generating a first reference signal in response to the first reference amount detected including averaging the first reference amount over time, the generating of the first detection signal further including scaling the first amount using the first reference signal;

determining whether the first amount exceeds a first prescribed threshold; and generating an alarm signal in event the first amount is determined to exceed the first prescribed threshold; and detecting an increased visibility condition including:

emitting infrared radiation away from the infrared emitter;

detecting a second amount of infrared radiation emitted during the second period of time having been backscattered by the airborne visibility impeding agent;

generating a second detection signal in response to the second amount of the infrared radiation;

detecting a second reference amount of said infrared radiation not having been backscattered by said airborne visibility impeding agent;

generating a second reference signal in response to the second reference amount detected;

determining whether the second amount is less than a second prescribed threshold, the second prescribed threshold being lower than the first prescribed threshold; and terminating the generating of the alarm signal in event the second amount is determined to be less than the second prescribed threshold.

15. The method of claim 14 wherein:

said generating of said second detection signal includes averaging said second amount over time; and said generating of said second reference signal includes averaging said second reference amount over time.

16. The method of claim 15 wherein:

said generating of said second detection signal includes: scaling said second amount using said second reference signal.

17. The method of claim 15 wherein said generating of said first detection signal includes:

determining whether said first reference amount is less than a reference threshold; and generating a fault signal in event said first reference amount is determined to be below the reference threshold.

18. A method for detecting an airborne visibility impeding agent comprising:

emitting infrared radiation away from an infrared emitter;

detecting an amount of the infrared radiation having been backscattered by the airborne visibility impeding agent;

generating a detection signal in response to the amount of the infrared radiation detected including averaging the amount of infrared radiation detected over time;

detecting a reference amount of the infrared radiation not having been backscattered by the airborne visibility impeding agent;

generating a reference signal in response to the reference amount including averaging the reference amount over time;

scaling the detection signal having been averaged using the reference signal;

determining whether the detection signal having been scaled exceeds a first prescribed threshold;

generating a first alarm signal in event the detection signal is determined to exceed the first prescribed threshold;

determining whether the detection signal exceeds a second prescribed threshold that is higher than the first prescribed threshold; and generating a second alarm signal in the event the detection signal is determined to exceed the second prescribed threshold.

19. The method of claim 18 wherein said generating of said detection signal includes:

determining whether said reference amount is less than a reference threshold; and generating a fault signal in event the reference amount is determined to be below the reference threshold.

20. The method of claim 18 including:

determining whether said detection signal is less than a first lower threshold;

terminating said generating of said first alarm signal in the event said detection signal is determined to be less than the first lower threshold;

determining whether said detection signal is less than a second lower threshold; and terminating said generating of said second alarm signal in the event said detection signal is determined to be less than the second lower threshold.

21. A method for detecting an airborne visibility impeding agent comprising:

emitting infrared radiation away from an infrared emitter;

detecting an amount of the infrared radiation having been backscattered by the airborne visibility impeding agent;

generating a backscatter signal in response to the amount of the infrared radiation detected;

detecting a reference amount of said infrared radiation not having been backscattered by said airborne visibility impeding agent;

generating a reference signal in response to the reference amount;

repeating the emitting, the detecting and the generating at least two times;

determining a running average of the backscatter signal over time;

determining a running average of the reference signal over time;

scaling said running average of said backscatter signal using said running average of said reference signal;

determining the amount of the infrared radiation having been backscattered as a function of the backscatter and determining whether the amount of the infrared radiation having been backscattered exceeds a prescribed threshold; and producing an alarm signal in event the running average, having been scaled, is determined to exceed the prescribed threshold.

22. The method of claim 21 including:

determining whether said running average is less than a lower threshold;

terminating said producing of said alarm signal in the event said running average is determined to be less than the lower threshold.

23. The method of claim 22 including:

determining whether said reference amount is less than a reference threshold; and generating a fault signal in event said reference amount is determined to be below the reference threshold.

* * * * *